(12) United States Patent  (10) Patent No.: US 12,390,807 B2
Hou et al.  (45) Date of Patent: Aug. 19, 2025

(54) CHIP LOADING STRUCTURE, ANALYSIS DEVICE, AND ANALYSIS SYSTEM

(71) Applicants: Beijing BOE Technology Development Co., Ltd., Beijing (CN); BOE TECHNOLOGY GROUP CO., LTD., Beijing (CN)

(72) Inventors: Mengjun Hou, Beijing (CN); Xiangguo Ma, Beijing (CN); Kai Geng, Beijing (CN); Qiong Wu, Beijing (CN); Youxue Wang, Beijing (CN); Zongmin Liu, Beijing (CN)

(73) Assignees: Beijing BOE Technology Development Co., Ltd., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 17/638,885

(22) PCT Filed: Apr. 29, 2021

(86) PCT No.: PCT/CN2021/090878
§ 371 (c)(1),
(2) Date: Feb. 28, 2022

(87) PCT Pub. No.: WO2022/226868
PCT Pub. Date: Nov. 3, 2022

(65) Prior Publication Data
US 2024/0042431 A1  Feb. 8, 2024

(51) Int. Cl.
*B01L 3/00* (2006.01)

(52) U.S. Cl.
CPC ... *B01L 3/502715* (2013.01); *B01L 2200/025* (2013.01); *B01L 2300/0816* (2013.01);
(Continued)

(58) Field of Classification Search
CPC ......... B01L 3/502715; B01L 2200/025; B01L 2300/0816; B01L 2300/0819;
(Continued)

(56) References Cited

U.S. PATENT DOCUMENTS

2004/0248318 A1* 12/2004 Weinberger ....... B01L 3/502715
422/68.1
2005/0221358 A1* 10/2005 Carrillo ................ G01N 21/648
435/6.16
(Continued)

FOREIGN PATENT DOCUMENTS

CN 201860420 U 6/2011
CN 106337021 A 1/2017
(Continued)

OTHER PUBLICATIONS

China Patent Office, First Office Action issued May 9, 2024 for application No. CN202180000986.0.
(Continued)

*Primary Examiner* — Jennifer Wecker
*Assistant Examiner* — Britney N. Washington
(74) *Attorney, Agent, or Firm* — HOUTTEMAN LAW LLC

(57) ABSTRACT

A chip loading structure, an analysis device and an analysis system are provided. The chip loading structure includes a loading plate body having therein an accommodating space adapted to accommodate a detection chip; a first hollow area and at least one second hollow area, which penetrate to the accommodating space, are disposed on a first plate surface of the loading plate body, the first hollow area being configured to expose a reaction observation area of the detection chip, the at least one second hollow area being configured to expose at least one reagent port of the detection chip; the loading plate body is further provided with a
(Continued)

connection portion which is detachably connectable to a transportation section in an analysis device, the transportation section being configured to transport the loading plate body.

20 Claims, 19 Drawing Sheets

(52) U.S. Cl.
CPC ............... *B01L 2300/0819* (2013.01); *B01L 2300/0829* (2013.01); *B01L 2300/1827* (2013.01); *B01L 2400/0487* (2013.01)

(58) Field of Classification Search
CPC ..... B01L 2300/0829; B01L 2300/1827; B01L 2400/0487; B01L 9/527; B01L 7/52; B01L 2200/147; B01L 2200/16; B01L 2300/027; B01L 2300/0645; B01L 2300/0654; B01L 2300/1844; B01L 2300/1894; C12M 1/00; C12M 1/36; C12M 1/42; G01N 35/04
See application file for complete search history.

(56) References Cited

U.S. PATENT DOCUMENTS

| | | | | |
|---|---|---|---|---|
| 2010/0216193 | A1* | 8/2010 | Gomi | B01L 3/50851 435/286.1 |
| 2014/0273187 | A1* | 9/2014 | Johnson | G01N 27/3272 435/287.2 |
| 2015/0224499 | A1* | 8/2015 | Wang | B01L 3/502715 435/7.1 |
| 2015/0328633 | A1* | 11/2015 | Yoo | C12Q 1/6851 435/6.12 |
| 2022/0099620 | A1* | 3/2022 | Chang | C12Q 1/686 |
| 2023/0160823 | A1* | 5/2023 | Hou | B01L 9/527 435/6.12 |

FOREIGN PATENT DOCUMENTS

| | | |
|---|---|---|
| CN | 107845949 A | 3/2018 |
| CN | 107904156 A | 4/2018 |
| CN | 108034703 A | 5/2018 |
| CN | 207904239 U | 9/2018 |
| CN | 109517731 A | 3/2019 |
| CN | 109517732 A | 3/2019 |
| CN | 109901056 A | 6/2019 |
| CN | 110066859 A | 7/2019 |
| CN | 110564607 A | 12/2019 |
| CN | 110672863 A | 1/2020 |
| CN | 209974747 U | 1/2020 |
| CN | 210128989 U | 3/2020 |
| CN | 110951610 A | 4/2020 |
| CN | 111458527 A | 7/2020 |
| CN | 111670253 A | 9/2020 |
| CN | 111812139 A | 10/2020 |
| CN | 111849758 A | 10/2020 |
| CN | 212180812 U | 12/2020 |
| CN | 212364335 U | 1/2021 |
| CN | 212560194 U | 2/2021 |
| CN | 112557684 A | 3/2021 |
| JP | 2018127261 A | 8/2018 |
| WO | 2020160335 A1 | 8/2020 |

OTHER PUBLICATIONS

Cai et al., "Advances of microfluidic technology in cell migration research," Biotechnology Bulletin, Mar. 26, 2010, vol. 3, pp. 73-75. English Abstract. DOI:10.13560/j.cnki.biotech.bull.1985.2010.03.011.

* cited by examiner

CHIP LOADING STRUCTURE, ANALYSIS DEVICE, AND ANALYSIS SYSTEM

TECHNICAL FIELD

Embodiments of the present disclosure relate to a chip loading structure, an analysis device, and an analysis system.

BACKGROUND

The digital polymerase chain reaction chip technology (dPCR) is to dilute a nucleic acid sample sufficiently to make the number of sample templates in each reaction cavity to be less than or equal to 1, so as to achieve absolute quantification of single-molecule DNA. Because of the advantages of high sensitivity, strong specificity, high detection flux, accurate quantification and the like, the method is widely applied to the aspects of clinical diagnosis, gene instability analysis, single cell gene expression, environmental microorganism detection, prenatal diagnosis and the like.

SUMMARY

At least one embodiment of the present disclosure provides a chip loading structure, which includes a loading plate body having an accommodating space configured to accommodate a detection chip;
 a first hollow area and at least one second hollow area, which penetrate to the accommodating space, are disposed on a first plate surface of the loading plate body; the first hollow area is configured to expose a reaction observation area of the detection chip, and the at least one second hollow area is configured to expose at least one reagent port of the detection chip; and
 the loading plate body is further provided with a connection portion which is detachably connectable to a transportation section in an analysis device, the transportation section being configured to transport the loading plate body.

Optionally, a first recess is disposed on the first plate surface at a position where the first hollow area is located, an area of an orthographic projection of the first recess on the first plate surface is larger than an area of an orthographic projection of the first hollow area on the first plate surface, and the orthographic projection of the first recess on the first plate surface completely covers the orthographic projection of the first hollow area on the first plate surface.

Optionally, a shape of the orthographic projection of the first hollow area on the first plate surface includes a square, a rectangle, or a circle.

Optionally, a plurality of second hollow areas are disposed by an interval along a first axis of the first plate surface, and in a case where the loading plate body is placed on the transportation section, a direction of the first axis is parallel to a first movement direction in which the transportation section moves into the analysis device.

Optionally, a second recess is disposed on the first plate surface at a position where each of the second hollow areas is located, an area of an orthographic projection of the second recess on the first plate surface is larger than an area of an orthographic projection of the second hollow area on the first plate surface, and the orthographic projection of the second recess on the first plate surface completely covers the orthographic projection of the second hollow area on the first plate surface Optionally, in a case where the loading plate body is placed on the transportation section, an area of an orthographic projection of a second recess, which is rearwardly located in the first movement direction, on the first plate surface is larger than an area of an orthographic projection of a second recess, which is forwardly located in the first movement direction, on the first plate surface;
 the orthographic projection of the second recess, which is rearwardly located in the first movement direction, on the first plate surface is of an oval shape; and the orthographic projection of the second recess, which is forwardly located in the first movement direction, on the first plate surface has a circular shape.

Optionally, the detection chip further has a heating electrode; and a third hollow area, which penetrates to the accommodating space, is disposed on the first plate surface to expose the heating electrode.

Optionally, the third hollow area extends to a first side edge of the first plate surface; and
 the first side edge is perpendicular to the first axis of the first plate surface; in a case where the loading plate body is placed on the transportation section, a direction of the first axis is parallel to a first movement direction in which the transportation section moves into the analysis device, and the first side edge is a side edge that is forwardly located in the first movement direction.

Optionally, a receiving groove is disposed on a second plate surface of the loading plate body opposite to the first plate surface to form the accommodating space, and a protrusion structure is disposed on an inner side surface of the receiving groove to confine the detection chip within the receiving groove.

Optionally, the protrusion structure includes two groups of protrusions distributed at opposite sides of the first axis of the first plate surface, each group of protrusions includes a plurality of protrusions spaced along the first axis, each protrusion protruding from the inner side surface of the receiving groove toward a direction approaching the first axis, so as to abut against a side surface of the detection chip in the receiving groove; and
 in a case where the loading plate body is placed on the transportation section, a direction of the first axis is parallel to a first movement direction in which the transportation section moves into the analysis device.

Optionally, a shape of an orthographic projection of the protrusion on the second plate surface includes a circular arc.

Optionally, the receiving groove extends to a second side edge of the second plate surface; and
 the second side edge is perpendicular to the first axis of the first plate surface; and in a case where the loading plate body is placed on the transportation section, a direction of the first axis is parallel to a first movement direction in which the transportation section moves into the analysis device, and the second side edge is a side edge that is forwardly located in the first movement direction.

Optionally, slot groups are respectively provided on two side surfaces at opposite sides of the first axis of the first plate surface of the loading plate body, each slot group including one or a plurality of slots spaced along the first axis, and the slots serve as the connection portion to be plugged with plug connectors in the transportation section in a one-to-one correspondence; and in a case where the loading plate body is placed on the transportation section, a direction of the first axis is parallel to a first movement direction in which the transportation section moves into the analysis device.

Optionally, a socket in communication with the slot is disposed on a second plate surface of the loading plate body opposite to the first plate surface to allow a corresponding plug connector to move into or out of the slot; a limiting protrusion is disposed on a side surface at a side of a second axis of the slot, and the limiting protrusion protrudes relative to the side surface toward a direction approaching the second axis, so as to confine the plug connector within the slot in a case where the plug connector moves to an interval position between the limiting protrusion and a bottom surface of the slot opposite to the limiting protrusion; and the second axis of the slot is parallel to a movement direction in which the plug connector moves into or out of the slot.

At least one embodiment of the present disclosure provides an analysis device, including: a loading section, a transportation section, a temperature control section and a signal detection section, the loading section adopts the chip loading structure provided by at least one embodiment of the present disclosure to carry a detection chip, and is detachably connectable to the transportation section;

the transportation section is configured to transport the chip loading structure;

the temperature control section includes a heater and a cooler, the heater is configured to heat the detection chip, and the cooler is configured to cool the detection chip; and the signal detection section includes an optical sensor configured to receive light from the detection chip and perform detection according to the light.

Optionally, the transportation section includes:

a transportation structure configured to bear the chip loading structure, and able to be at least partially driven;

a driver configured to drive the transportation structure to cause the chip loading structure to reciprocate among a first position, a second position, and a third position, the first position allows the chip loading structure to be received in the transportation structure;

the second position allows the temperature control section to adjust a temperature of the detection chip; and the third position allows the optical sensor of the signal detection section to receive the light from the detection chip.

Optionally, the transportation structure includes: an objective table configured to, in use, bear the chip loading structure;

a movable platform configured to be connected to the driver to move under drive of the driver; and a support configured to connect the objective table and the movable platform, so that the objective table is driven along with the movable platform.

Optionally, the loading section adopts the chip loading structure provided by at least one embodiment of the present disclosure;

a mounting groove adapted to accommodate the loading plate body is disposed on a bearing surface of the objective table, and a mounting groove opening in communication with the mounting groove is disposed on a first side surface of the objective table to allow the loading plate body to move into or out of the mounting groove, the first side surface being perpendicular to a first movement direction in which the objective table moves into the analysis device, and the first side surface is a side surface facing backwards in the first movement direction;

and, the plug connectors, which protrude from the side surface of the mounting groove toward a direction approaching a third axis of the mounting groove, are disposed on the objective table, the third axis being parallel to the first movement direction.

Optionally, the loading section adopts the chip loading structure provided by at least one embodiment of the present disclosure;

the heater includes at least one contact electrode configured to, in use, be in electrical contact with the at least one heating electrode of the detection chip in one-to-one correspondence;

the heater is further configured to apply an electrical signal to the heating electrode of the detection chip through the contact electrode, so that the heating electrode heats the detection chip.

Optionally, the contact electrode is fixed on a bearing surface of the objective table and is located at a side of the mounting groove opposite to the mounting groove opening, and one end of the contact electrode protrudes relative to a side surface of the mounting groove in a direction opposite to a first movement direction in which the objective table moves into the analysis device;

the contact electrode is provided with a contact portion which is adapted to be in electrical contact with the heating electrode, the contact portion protrudes relative to a surface of the contact electrode opposite to the heating electrode toward a direction approaching the heating electrode; and the heater further includes an elastic piece, which is respectively connected to the contact electrode and the objective table, to apply a pulling force to the contact electrode toward the bearing surface of the objective table.

Optionally, the elastic piece includes a spring.

Optionally, an electrode slot is provided on a bearing surface of the objective table, the contact electrode is inserted in the electrode slot, and the contact electrode is fixedly connected to the objective table by a fastener.

Optionally, the signal detection unit further includes:

a light source configured to, in use, provide light to illuminate the detection chip;

a light transmission portion configured to, in use, transmit the light provided by the light source to the detection chip and transmit light emitted by the detection chip to the optical sensor; and a bracket configured to fix and bear the light source and the light transmission portion, wherein a focal length adjustment structure is disposed on the bracket and configured to adjust a distance between the light transmission portion and the detection chip, such that the detection chip is positioned at a focus of the light transmission portion; and the focal length adjustment structure has a focal length adjustment knob and a knob extension connected to the focal length adjustment knob, the knob extension extending to a side close to the light transmission portion to facilitate manual adjustment.

At least one embodiment of the present disclosure also provides an analysis system, including:

the above-mentioned analysis device provided by at least one embodiment of the present disclosure; and the detection chip.

BRIEF DESCRIPTION OF DRAWINGS

To illustrate the technical solutions of the embodiments of the present disclosure more clearly, the drawings of the embodiments will be briefly introduced below, and it is apparent that the drawings described below only relate to some embodiments of the present disclosure and are not intended to limit the present disclosure.

DETAIL DESCRIPTION OF EMBODIMENTS

Figure 1:
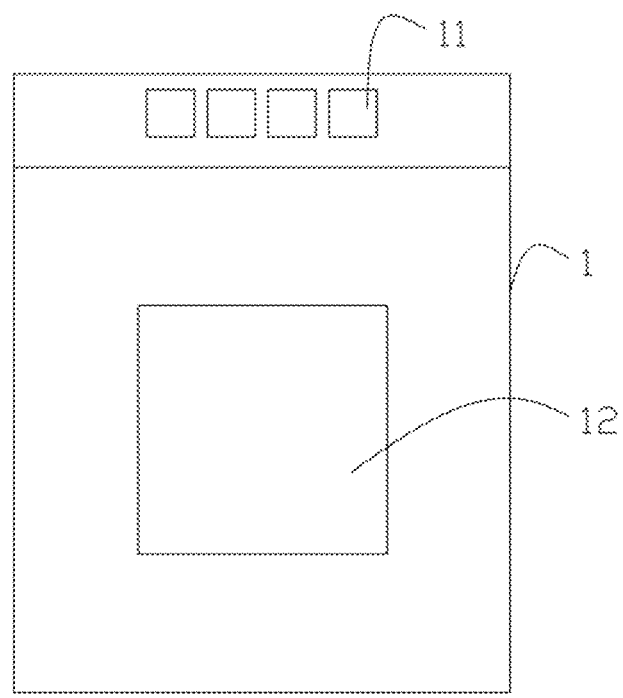
FIG. 1 is a schematic block diagram of a detection chip according to at least one embodiment of the present disclosure.

To make the objects, technical solutions and advantages of the embodiments of the present disclosure more apparent, the technical solutions of the embodiments of the present disclosure will be described clearly and completely below with reference to the drawings of the embodiments of the present disclosure. It should be understood that the described embodiments are not all of but only a few embodiments of the present disclosure. All other embodiments, which can be derived by a person skilled in the art from the described embodiments of the disclosure without inventive labor, are within the scope of protection of the disclosure.

Unless defined otherwise, technical or scientific terms used herein shall have the ordinary meaning as understood by one of ordinary skill in the art to which this disclosure belongs. The use of "first," "second", and the like in this disclosure is not intended to indicate any order, quantity, or importance, but rather is used to distinguish one component from other components. The word "comprising" or "including", and the like, means that the element or item preceding the word comprises the element or item listed after the word and its equivalent, but does not exclude other elements or items. The terms "connected" or "coupled" and the like are not restricted to physical or mechanical connections, but may include electrical connections, whether direct or indirect. The terms "upper", "lower", "left", "right", and the like are used only to indicate relative positional relationships, and when the absolute position of the object being described is changed, the relative positional relationships may also be changed accordingly.

To maintain the following description of the embodiments of the present disclosure clear and concise, detailed description of known functions and known components is omitted from the present disclosure.

Some dPCR products generally require multiple sets of equipment to obtain an analysis result, which results in long detection time, high detection cost, multiple operating steps, and the risk of reagent contamination.

At least one embodiment of the present disclosure provides a chip loading structure, an analysis device, and an analysis system. The analysis device of the embodiment combines and integrates a loading section, a temperature control section, and a signal detection section, and realizes detection of a detection chip with a single device, thereby reducing the number of auxiliary equipments required, simplifying the operation steps, shortening the detection time, and reducing the risk of reagent contamination. In addition, by using the above chip loading structure to carry the detection ship and detachably connecting the chip loading structure to the transportation section in the analysis device, not only the detection chip can be protected from the risk of being damaged in the process of being placed into the transportation section, but also the process of loading or unloading the detection chip into or from the transportation section can be simplified, thereby increasing the loading convenience of the detection chip.

FIG. 1 is a schematic block diagram of a detection chip according to at least one embodiment of the present disclosure. As shown in FIG. 1, one side of the detection chip 1 has a reaction observation area 12, for example, in the case of a microfluidic chip such as a digital polymerase chain reaction chip (dPCR), the reaction observation area 12 is, for example, an area of micropore reaction chamber array. The detection chip 1 further has heating electrodes 11, each of which has, for example, a rectangular plate shape. Upon receiving an electrical signal, the heating electrode 11 or a component such as a resistive trace electrically connected to the heating electrode 11 may generate heat to heat the detection chip 1. Of course, in practical applications, depending on the type of detection chip, a detection chip 1 without a heating electrode may also be provided. In addition, the detection chip 1 may also include electrodes for other purposes, such as electrodes for applying an electric signal to drive the sample to move in the detection chip 1, and the like. As described above, the type, structure, and the like of the detection chip 1 are not limited in the embodiments of the present disclosure.

It should be understood that the detection chip 1 described in the embodiments of the present disclosure may be any type of biological detection chip or chemical detection chip, such as various microfluidic chips, which is not limited in the embodiments of the present disclosure.

Figure 2A:
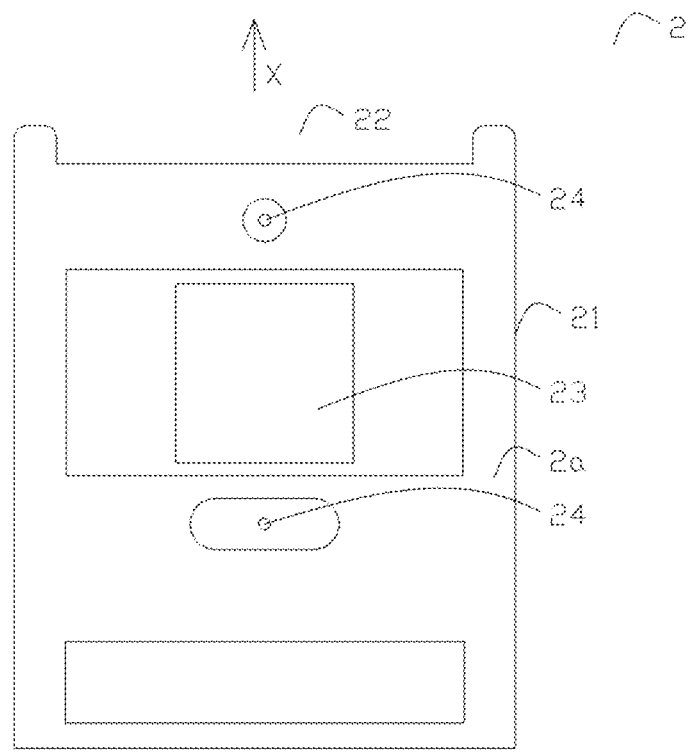
FIG. 2A is a front structural view of a chip loading structure according to at least one embodiment of the present disclosure.
Figure 2B:
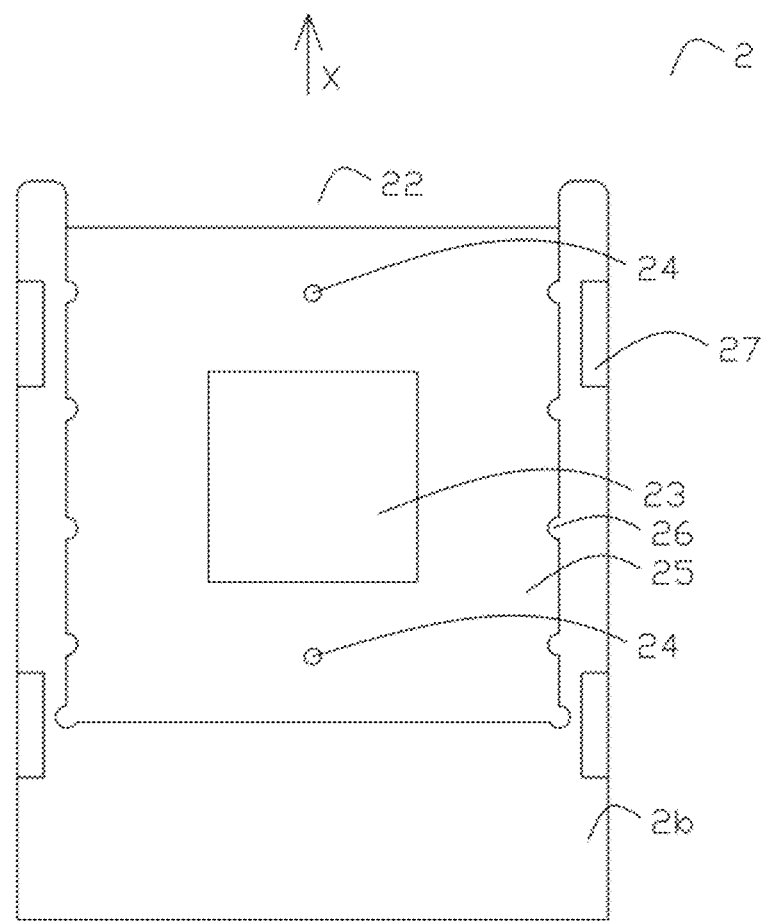
FIG. 2B is a back structural view of a chip loading structure according to at least one embodiment of the present disclosure.
Figure 2C:
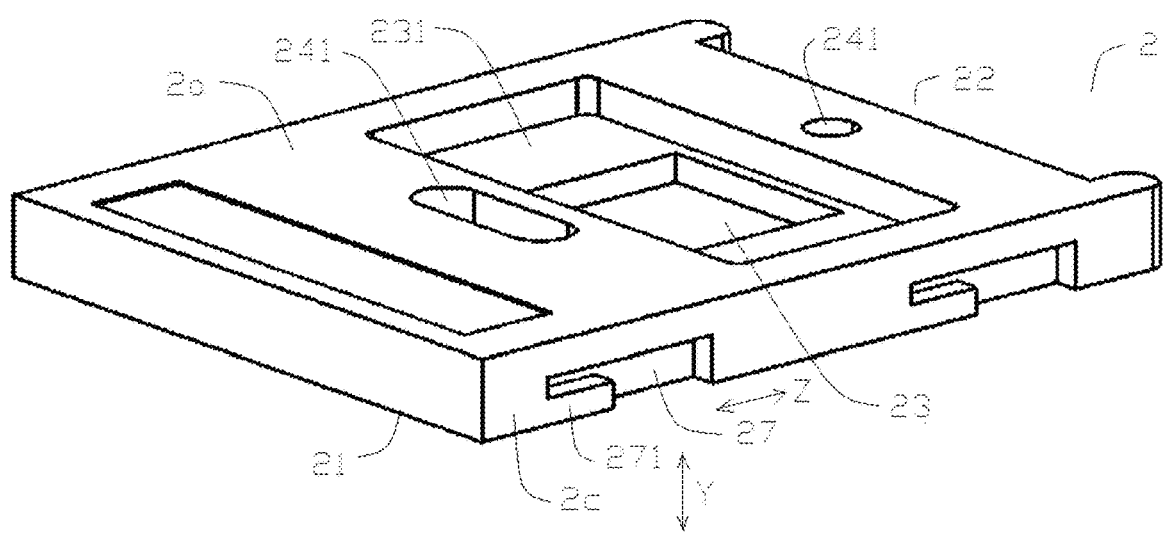
FIG. 2C is a perspective view of a chip loading structure according to at least one embodiment of the present disclosure.

FIG. 2A is a front structural view of a chip loading structure according to at least one embodiment of the present disclosure. FIG. 2B is a back structural view of a chip loading structure according to at least one embodiment of the present disclosure. FIG. 2C is a perspective view of a chip loading structure according to at least one embodiment of the present disclosure. Referring to FIGS. 2A to 2B, the chip loading structure 2 according to at least one example of the present disclosure may be detachably connected to a transportation section in an analysis device, so as to not only protect the detection chip 1 from being damaged in the process of being placed in the transportation section, but also simplify the process of loading or unloading of the detection chip 1 into or from the transportation section, thereby improving the loading convenience of the detection chip 1.

Figure 2D:
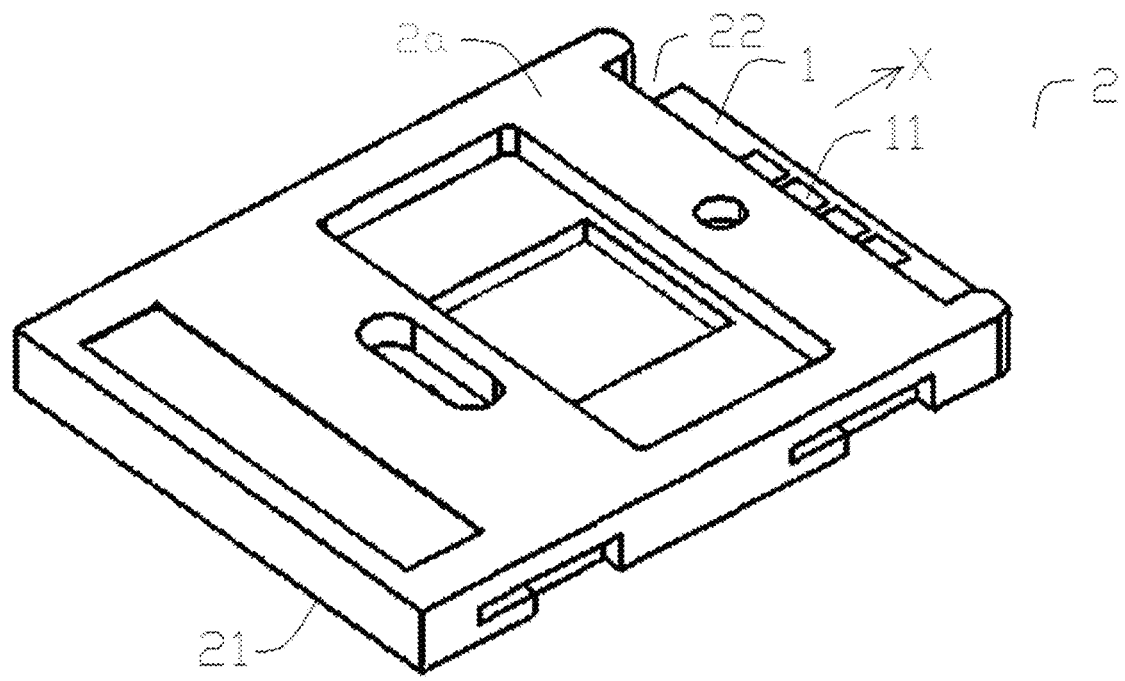
FIG. 2D is a perspective view of a chip loading structure carrying a detection chip according to at least one embodiment of the present disclosure.

Specifically, the chip loading structure 2 includes a loading plate body 21, which is, for example, a rectangular plate and is, optionally, made of a high temperature resistant material, so as to ensure that the detection chip 1 is not deformed when being heated. The loading plate body 21 is a rectangular box as a whole, and generally has an outline substantially the same as the shape of the detection chip 1. The loading plate body 21 has an accommodating space configured to accommodate the detection chip 1. For example, as shown in FIG. 2D, the detection chip 1 is located in the accommodating space.

As shown in FIG. 2A, a first hollow area 23 and at least one second hollow area 24, which penetrate to the accommodating space, are disposed on a first plate surface 2a of the loading plate body 21. For example, two second hollow areas 24 are shown in FIGS. 2A and 2B. The first hollow area 23 is configured to expose the reaction observation area 12 of the detection chip 1; and the respective second hollow areas 24 are configured to expose respective reagent ports (not shown in the figure) of the detection chip 1. Optionally, as shown in FIG. 2C, a first recess 231 may be further disposed on the first plate surface 2a of the loading plate body 21 at a position where the first hollow area 23 is located, an area of an orthographic projection of the first recess 231 on the first plate surface 2a is larger than an area of an orthographic projection of the first hollow area 23 on the first plate surface 2a, and the orthographic projection of the first recess 231 on the first plate surface 2a completely covers the orthographic projection of the first hollow area 23 on the first plate surface 2a. By providing the first recess 231, the observation field of view can be enlarged.

Figure 2E:
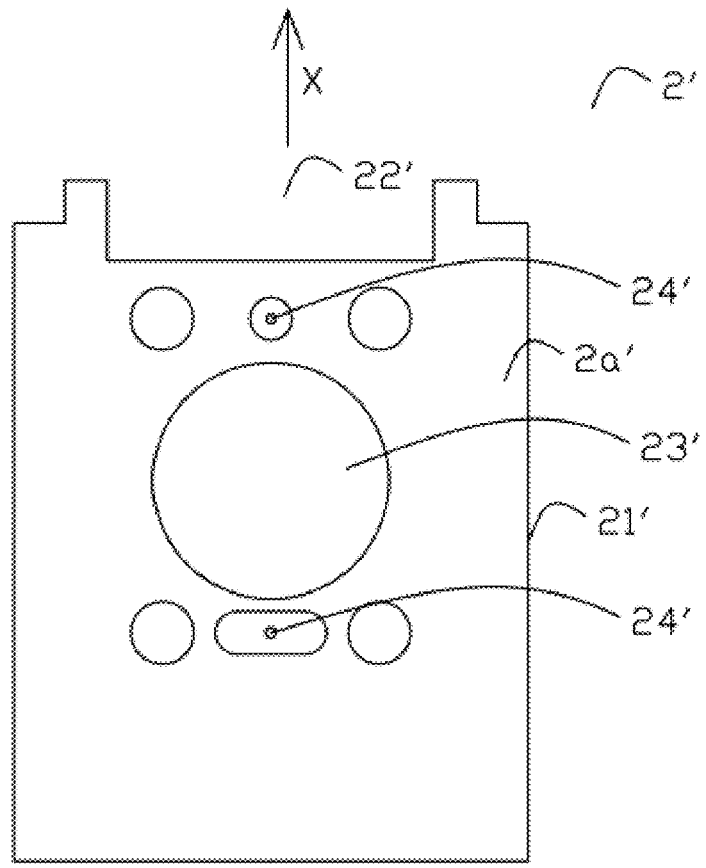
FIG. 2E is a front structural view of another chip loading structure according to at least one embodiment of the present disclosure.
Figure 2F:
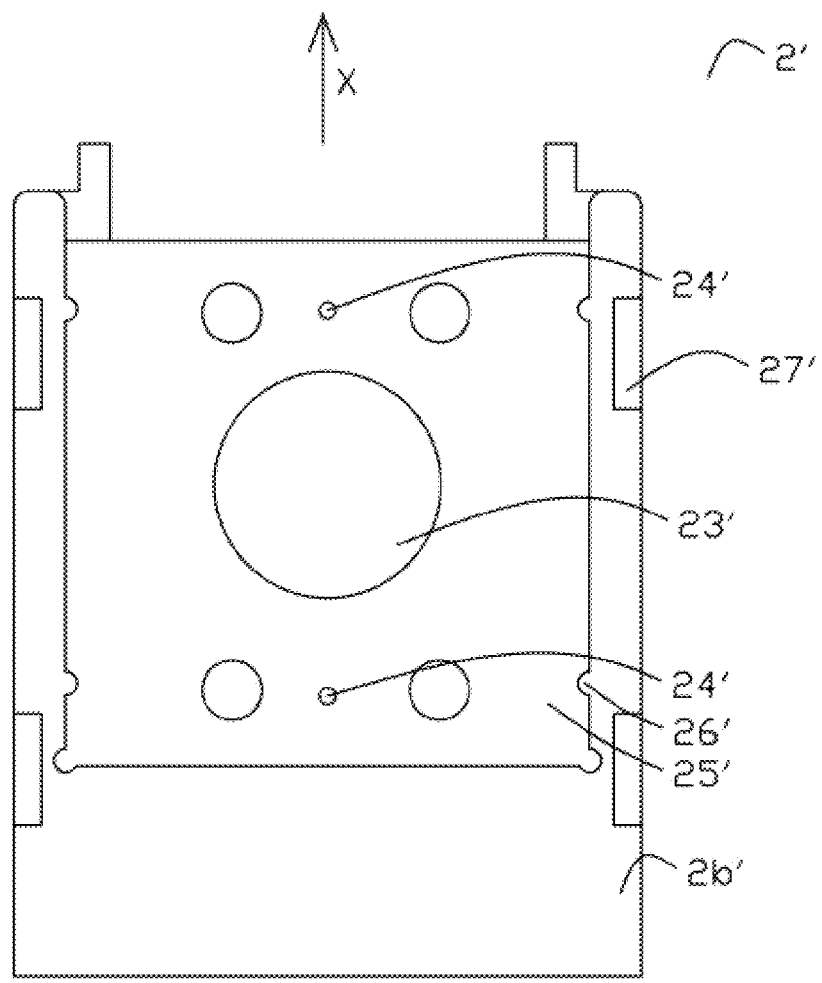
FIG. 2F is a back structural view of another chip loading structure according to at least one embodiment of the present disclosure.

In some embodiments, optionally, the orthographic projection of the first hollow area 23 on the first plate surface 2a has a shape selected from a group consisting of square, rectangle and circle. For example, FIG. 2A shows that the shape of the orthographic projection of the first hollow area 23 on the first plate surface 2a is a square. For another example, as shown in FIG. 2E, an embodiment of the disclosure further provides another chip loading structure 2', in which a first hollow area 23' is disposed on a first plate surface 2a' of a loading plate body 21', and the shape of the orthographic projection of the first hollow area 23' on the first plate surface 2 a' is a circle. It should be noted that, in practical applications, detection chips 1 of different types and structures may be equipped with corresponding chip loading structures.

In some embodiments, optionally, a plurality of second hollow areas 24 are disposed by an interval along a first axis of the first plate surface 2a. In a case where the loading plate body is placed on the transportation section, a direction of the first axis is parallel to a first movement direction in which the transportation section moves into the analysis device (i.e., direction X shown in FIG. 2A). For example, FIGS. 2A and 2B show two second hollow areas 24, which are disposed by an interval along the direction X and are located at opposite sides of the first hollow area 23, respectively. Of course, in practical applications, the two second hollow areas 24 may also be located on the same side of the first hollow area 23.

In some embodiments, optionally, as shown in FIG. 2C, a second recess 241 may be disposed on the first plate surface 2a of the loading plate body 21 at a position where each of the second hollow areas 24 is located. An area of an orthographic projection of the second recess 241 on the first plate surface 2a is larger than an area of an orthographic projection of the second hollow area 24 on the first plate surface 2a, and the orthographic projection of the second recess 241 on the first plate surface 2a completely covers the orthographic projection of the second hollow area 24 on the first plate surface 2a. By disposing the second recesses 241, the reagent can be prevented from leaking when being filled or discharged.

In some embodiments, optionally, as shown in FIG. 2A, in a case where the loading plate body 21 is placed on the transportation section, an area of an orthographic projection of the second recess 241, which is rearwardly located in the first movement direction (i.e., the direction X shown in FIG. 2A), on the first plate surface 2a is larger than an area of an orthographic projection of the second recess 241, which is forwardly located in the first movement direction, on the first plate surface 2a. This is because: for some detection chips, such as the detection chip 1 shown in FIG. 1, a reagent filling port among the plurality of reagent ports is generally located at a position rearward in the first movement direction (i.e., the direction X shown in FIG. 2A), while the reagent discharge port is generally located at a position forward in the first movement direction (i.e., the direction X shown in FIG. 2A), and when the reagent is filled the reagent is more likely to leak from the reagent filling port than from the reagent discharge port. Therefore, the reagent can be further prevented from leaking by appropriately increasing the area of the orthographic projection of the second recess 241 corresponding to the reagent filling port on the first plate surface 2a. Optionally, the orthographic projection of the second recess 241, which is rearwardly located in the first movement direction, on the first plate surface 2a is of an oval shape; the orthographic projection of the second recess 241, which is forwardly located in the first movement direction, on the first plate surface 2a has a circular shape.

In the embodiment of the present disclosure, the detection chip 1 further has at least one heating electrode 11. In order to achieve electrical contact of the heating electrode with a contact electrode (described in detail below) in the heater, as shown in FIG. 2D, a third hollow area 22 penetrating to the accommodating space is disposed on the first plate surface 2a of the loading plate body 21 to expose the heating electrode 11. In such way, the contact electrode may electrically contact the heating electrode 11 through the third hollow area 22 from a side of the first plate surface 2a of the loading plate body 21. Optionally, as shown in FIG. 2D, in order to facilitate electrical contact of the third hollow area 22 with the heating electrode 11, the third hollow area 22 extends to a first side edge of the loading plate body 21, and the first side edge is perpendicular to the first axis of the first plate surface 2a. When the loading plate body 21 is placed on the transporting section, a direction of the first axis is parallel to the first movement direction (i.e., the direction X shown in FIG. 2D), and the first side edge is the side edge that is forwardly located in the first movement direction.

It should be noted that, an embodiment of the present disclosure also provides another chip loading structure 2', which also has a second hollow area 24' and a third hollow area 22' disposed on the first plate surface 2a' of the loading plate body 21'. Since the arrangement manner of the second hollow area 24' and the third hollow area 22' is the same as that of the second hollow area 24 and the third hollow area 22, the description is omitted here.

It should be noted that, in practical applications, the number and positions of the reagent ports of the detection chip 1 may be different depending on different types. The number and positions of the second hollow areas 24 in the embodiment of the present disclosure may be adaptively designed according to the number and positions of the reagent ports of the detection chip 1. In addition, according to different types of detection chips 1, hollow areas with other functions may also be disposed on the first plate surface 2a of the loading plate body 21, which is not limited in the embodiments of the present disclosure.

In some embodiments of the present disclosure, the structure of the accommodating space may be various. For example, as shown in FIG. 2B, a receiving groove 25 is disposed on a second plate surface 2b of the loading plate body 21 opposite to the first plate surface 2a to construct the accommodating space. Because the receiving groove 25 is open on the second plate surface 2b, the detection chip 1 can move in or out of the receiving groove 25 from the side of the second plate surface 2b. Meanwhile, a open receiving groove 25 is helpful for improving the cooling efficiency of the detection chip 1 and preventing the temperature of the loading plate body 21 from being too high. Also, a protrusion structure is disposed on an inner side surface of the receiving groove 25 to confine the detection chip 1 within the receiving groove 25.

The protrusion structure may have various structures. For example, as shown in FIG. 2B, the protrusion structure includes two groups of protrusions distributed at opposite sides of the first axis (parallel to the direction X) of the first plate surface 2a. Each group of protrusions includes a plurality of protrusions 26 spaced along the first axis, and each protrusion 26 protrudes from the inner side surface of the receiving groove 25 toward a direction approaching the first axis to abut against the side surface of the detection chip 1 placed in the receiving groove 25, so that the detection chip 1 can be fixed in the receiving groove 25 under friction. Such protrusion structure can not only reduce the contact area with the detection chip 1 to facilitate installation of detection chip 1, but also ensure fixation stability due to the detection chip 1 being clamped by the two groups of protrusions at both sides of the detection chip 1. Optionally, in order to avoid scratch and abrasion between the detection chip 1 and the protrusion 26, the shape of the orthographic projection of the protrusion 26 on the second plate surface 2b is designed to be a circular arc such as a semicircle or a semi-ellipse.

In some embodiments, optionally, the receiving groove 26 extends to a second side edge of the second plate surface 2b; the second side edge is perpendicular to the first axis (parallel to the direction X), and the second side edge is a side edge that is forwardly located in the first movement direction. In this way, for the detection chip 1 provided with the heating electrode 11, in a case where the loading plate body 21 is placed on the transportation section, the position of the heating electrode 11 can correspond to the position of the contact electrode on the transportation section to achieve contact connection between the heating electrode and the contact electrode.

It should be noted that, an embodiment of the present disclosure further provides another chip loading structure 2', which also has a receiving groove 25' and a protrusion structure 26' disposed on the second plate surface 2b' of the loading plate body 21'. Since the arrangement manner of the receiving groove 25' and the protrusion structure 26' is the same as that of the receiving groove 25 and the protrusion structure 26, therefore description is omitted here.

In some embodiments of the present disclosure, as shown in FIGS. 2B and 2C, a connection portion 27 is further disposed on the loading plate body 21, the connection portion 27 being detachably connectable to a transportation section in the analysis device, and the transportation section being configured to transport the loading plate body 21. That is to say, the detection chip 1 is not directly installed on the transportation section, but is installed on the transportation section with the aid of the loading plate body 21, so that not only the detection chip 1 can be protected from being damaged in the process of being placed into the transportation section, but also the process of loading and unloading of the detection chip 1 on and from the transportation section can be simplified, thereby increasing the loading convenience of the detection chip.

The connection portion 27 may be connected to the transportation section, for example, in a plug-connection manner. Specifically, as shown in FIGS. 2B and 2C, slot groups are disposed on both side surfaces 2c of the loading plate body 21 with respect to the first axis (i.e. parallel to the X-direction). Each slot group includes one or a plurality of slots spaced along the first axis, and the slots serve as the connection portion 27. For example, as shown in FIG. 2C, each slot group disposed on each side face 2C includes two slots (i.e., the connection portion 27), and the respective slots are plugged with plug connectors (described later) in the transportation section in one-to-one correspondence, so that the loading plate body 21 is detachably fixed on the transportation section. Meanwhile, such plug-connection is very convenient, which simplifies the process of loading and unloading of the detection chip 1 on and from the transportation section, thereby improving the installation efficiency. Of course, in practical applications, the connection portion 27 may be connected to the transportation section in any other detachable manner, such as clamping, mechanical fixing, etc.

In some embodiments of the present disclosure, optionally, as shown in FIG. 2B, a socket in communication with the slot is disposed on the second plate surface 2b of the loading plate body 21 opposite to the first plate surface 2a, so as to allow a corresponding plug connector to move into or out of the slot. For example, as shown in FIG. 2C, the socket of the slot faces downward, and the plug connector can move into or out of the slot through the socket along the direction Y. Further, a limiting protrusion 271 is disposed on a side surface of the slot at a side of the second axis (parallel to the direction Y), and the limiting protrusion 271 protrudes relative to the side surface toward a direction approaching the second axis, such that the plug is confined within the slot when the plug in the slot moves relative to the loading plate body 21 to an interval position between the limiting protrusion 271 and a bottom surface of the slot opposite to the limiting protrusion 271.

When the loading plate body 21 needs to be installed, as shown in FIG. 2C, the loading plate body 21 is firstly moved downward along the direction Y to move the plug connector into the slot through the socket along the direction Y; then the loading plate body 21 is translated rightward along the direction Z to translate the plug connector leftward along the direction Z to above the limiting protrusion 271, that is, to an interval position between the limiting protrusion 271 and a bottom surface of the slot opposite to the limiting protrusion 271. At this time, with the cooperation of the limiting protrusion 271 and the plug connector, the loading plate body 21 is immovable along the direction Y, that is, the loading plate body 21 is fixed on the transportation section. Conversely, when the loading plate body 21 needs to be unloaded, the loading plate body 21 is firstly translated leftward along the direction Z to translate the plug connector rightward along the direction Z to a position which is staggered with the limiting protrusion 271 and opposite to the socket; then, the loading plate body 21 is moved upward in the direction Y to move the plug connector out of the slot through the socket in the direction Y. At this time, the loading plate body 21 can move in the direction Y, that is, the loading plate body 21 can be unloaded from the transportation section.

It should be noted that, the embodiment of the present disclosure further provides another chip loading structure 2', which also has a connection portion 27' disposed on the second plate surface 2b' of the loading plate body 21'. Since the arrangement manner of connection portion 27' is the same as the connection portion 27, the description is omitted here.

Figure 3:
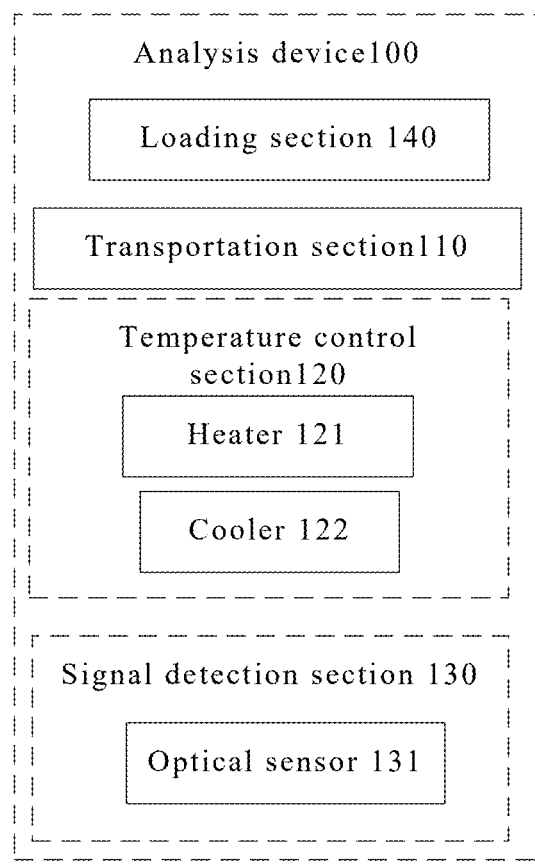
FIG. 3 is a schematic block diagram of an analysis device according to at least one embodiment of the present disclosure.

At least one embodiment of the present disclosure provides an analysis device. FIG. 3 is a schematic block diagram of an analysis device according to at least one embodiment of the present disclosure. As shown in FIG. 3, an analysis device 100 according to at least one embodiment of the present disclosure may include at least a loading section 140, a transportation section 110, a temperature control section 120, and a signal detection section 130.

The transportation section 110 adopts the chip loading structure provided by at least one embodiment of the present disclosure. The transportation section 110 is configured to carry the detection chip 1 and is detachably connectable to the transportation section 110.

The transportation section is configured to transport the chip loading structure. The transportation section 110 is configured to, in use, receive and bear the loading plate body 21 (bearing the detection chip 1) in the chip loading structure, and allow the loading plate body 21 to move to the temperature control section 120 and the signal detection section 130.

The temperature control section 120 includes a heater 121 and a cooler 122. The heater 121 is configured to heat the detection chip 1 (carried by the loading plate body 21) loaded into the analysis device, and the cooler 122 is configured to cool down the detection chip 1 loaded into the analysis device, thereby achieving temperature control of the detection chip 1.

The signal detection section 130 includes an optical sensor 131, which is configured to receive light from the detection chip 1 and perform detection according to the light of the detection chip 1.

Figure 4:
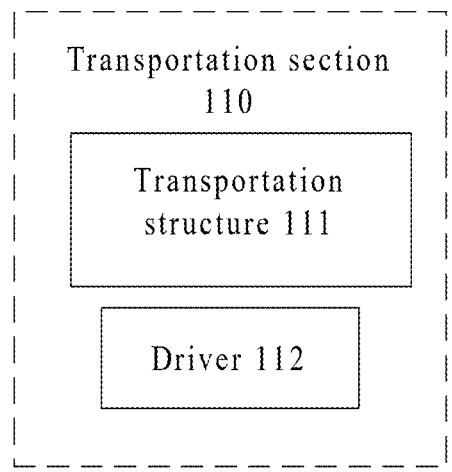
FIG. 4 is a schematic block diagram of a transportation section according to at least one embodiment of the present disclosure.

FIG. 4 is a schematic block diagram of a transportation section according to at least one embodiment of the present disclosure. The transportation section 110 may include a transportation structure 111 and a driver 112.

The transportation structure 111 is configured to bear the chip loading structure (i.e., the loading plate body 21), and can be at least partially driven. The driver 112 is configured to drive the transportation structure 111, for example, to be operably connected with the transportation structure 111 to cause the chip loading structure (i.e., the loading plate body 21) to reciprocate among a first position, a second position, and a third position. In at least one embodiment, the first position allows the chip loading structure (i.e., the loading plate body 21) to be received in the transportation structure 111, i.e., allows a user to put the loading plate body 21 into the transportation section 110, causing the loading plate body 21 to carry the detection chip 1 loaded with a detection sample. The second position allows the temperature control section 120 to adjust the temperature of the detection chip 1. The third position allows the optical sensor 131 of the signal detection section 130 to receive light from the detection chip 1. For example, an example of the first position in at least one embodiment of the present disclosure is shown in FIG. 12B, which will be described below. For example, an example of the second position in at least one embodiment of the present disclosure is shown in FIG. 12C, which will be described below. For example, an example of the third position in at least one embodiment of the present disclosure is shown in FIG. 12D, which will be described below.

However, it should be understood that in some embodiments, the transportation section 110 may not include the driver 112, such that the transportation structure 111 may be manually moved (e.g., be pushed or pulled), which is not limited in the embodiments of the present disclosure.

Figure 5A:
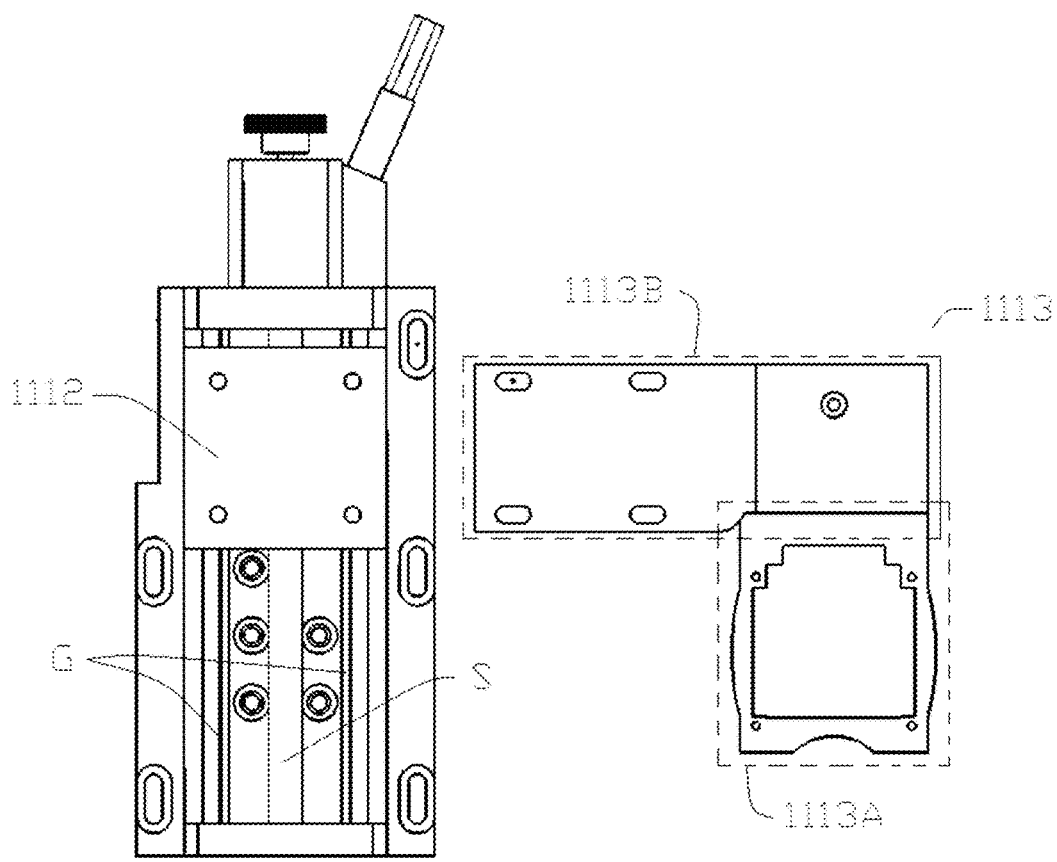
FIG. 5A is a block diagram of a transportation structure in an exploded state according to at least one embodiment of the present disclosure.
Figure 5B:
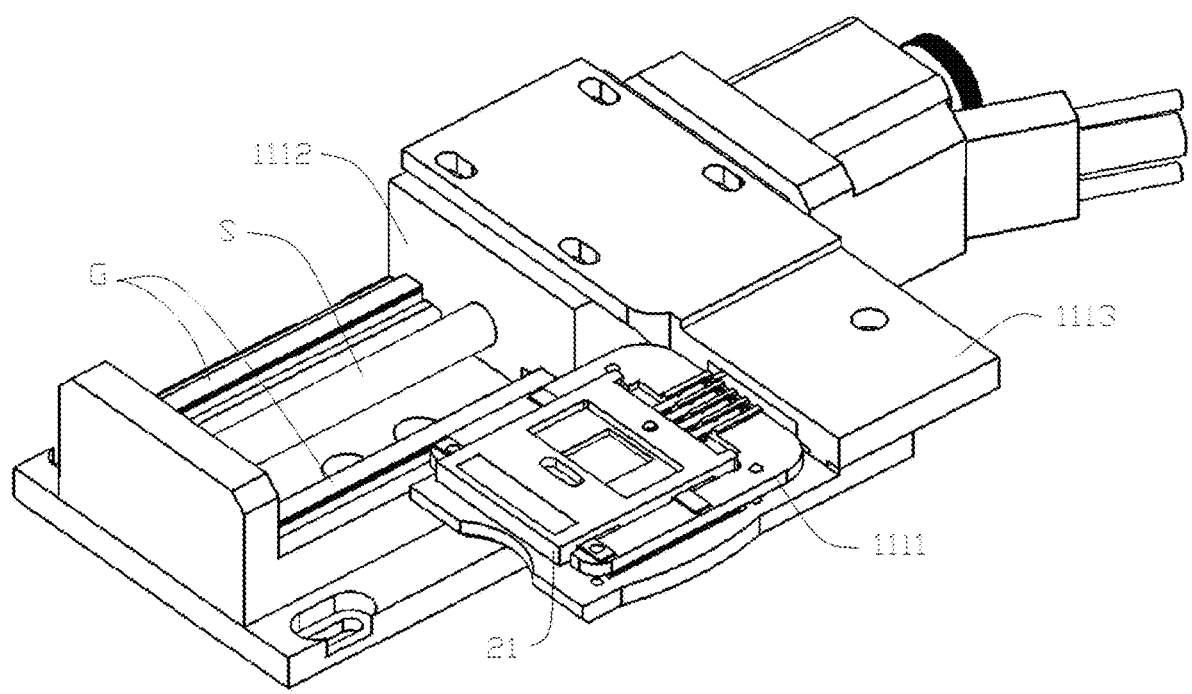
FIG. 5B is a block diagram of a transportation structure in an assembled state according to at least one embodiment of the present disclosure.

FIG. 5A is a structural view of a transportation structure in an exploded state according to at least one embodiment of the present disclosure, and FIG. 5B is a structural view of a transportation structure in an assembled state according to at least one embodiment of the present disclosure. As shown in FIGS. 5A and 5B, the transportation structure 111 may include an objective table 1111, a movable platform 1112, and a support 1113.

Figure 6A:
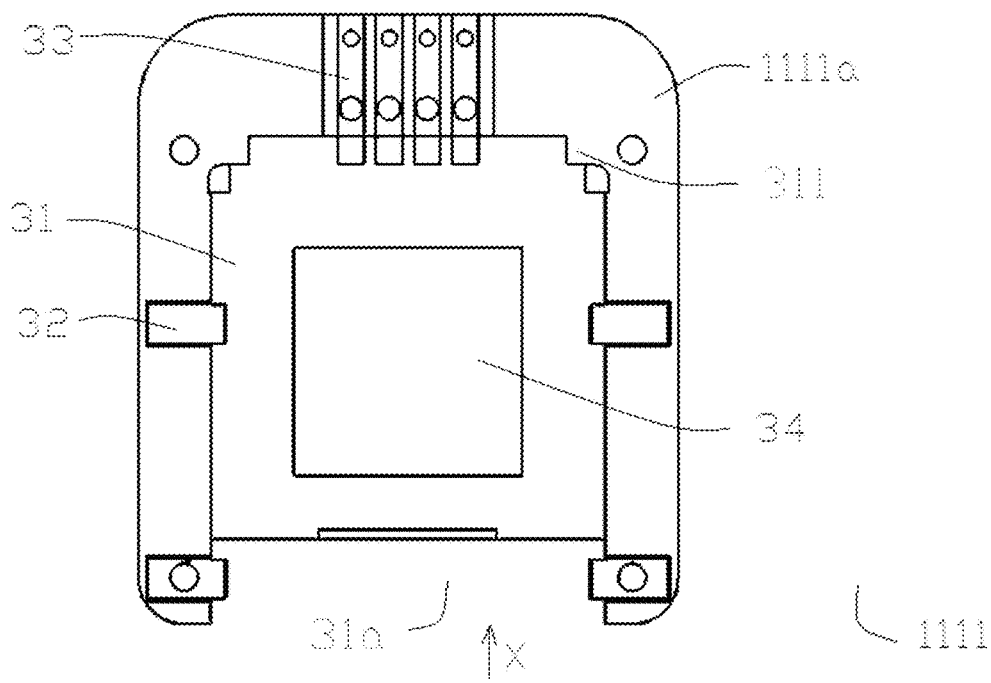
FIG. 6A is a front structural view of an objective table according to at least one embodiment of the present disclosure.

The objective table 1111 is configured to, in use, bear the chip loading structure (i.e., the loading plate body 21) described above. In the example shown in FIGS. 6A to 6E, the objective table 1111 has a rectangular plate shape, and is movably mounted on the support 1113 (as shown in FIG. 5B). FIG. 6A is a front structural view of an objective table according to at least one embodiment of the present disclosure. As shown in FIG. 6A, the objective table 1111 may be connected to the connection portion 27 of the loading plate body 21 in the chip loading structure in a plug-connection manner. Specifically, a mounting groove 31 adapted to accommodate the loading plate body 21 is disposed on a loading surface 1111a of the objective table 1111, and a mounting groove opening 31a in communication with the mounting groove 31 is disposed at a first side surface of the objective table 1111 for the loading plate body 21 to move into or out of the mounting groove 31. As shown in FIG. 6A, the first side surface is perpendicular to a first movement direction (i.e., direction X shown in FIG. 6A) in which the objective table 1111 moves into the analysis device, and is a side surface facing backward in the first movement direction.

A plug connector 32, which protrudes relative to the side surface of the mounting groove 31 toward a direction approaching a third axis (parallel to the direction X) of the mounting groove 31, is further disposed on the objective table 1111. In association with in FIGS. 2C and 6E, the portion of the plug connector 32 that protrudes relative to the side surface of the mounting groove 31 can move through the socket into or out of the slot (i.e., the connection portion 27) in the direction Y. It should be understood that, by means of the mounting groove opening 31a, the loading plate body 21 placed in the mounting groove 31 may be allowed to translate in the direction X, so as to translate the plug connector 32 rightward or leftward in the direction Z shown in FIG. 2C. Since the plug-connection of the plug connector 32 and the slot have been described in detail above, description thereof is omitted here.

In some embodiments of the present disclosure, optionally, the objective table 1111 may be formed of a high temperature resistant material, which may be, for example, metal, plastic, ceramic, rubber, resin, etc. The thermal deformation temperature of the high temperature resistant material forming the objective table 1111 may be, for example, 100° C., 200° C., 300° C., 400° C., 500° C. or higher. The objective table 1111 may also be formed of a material resistant to high temperature but poor in thermal conductivity. For example, in one particular embodiment, the objective table 1111 may be formed of ceramic to provide both light weight and high temperature resistance.

Figure 6B:
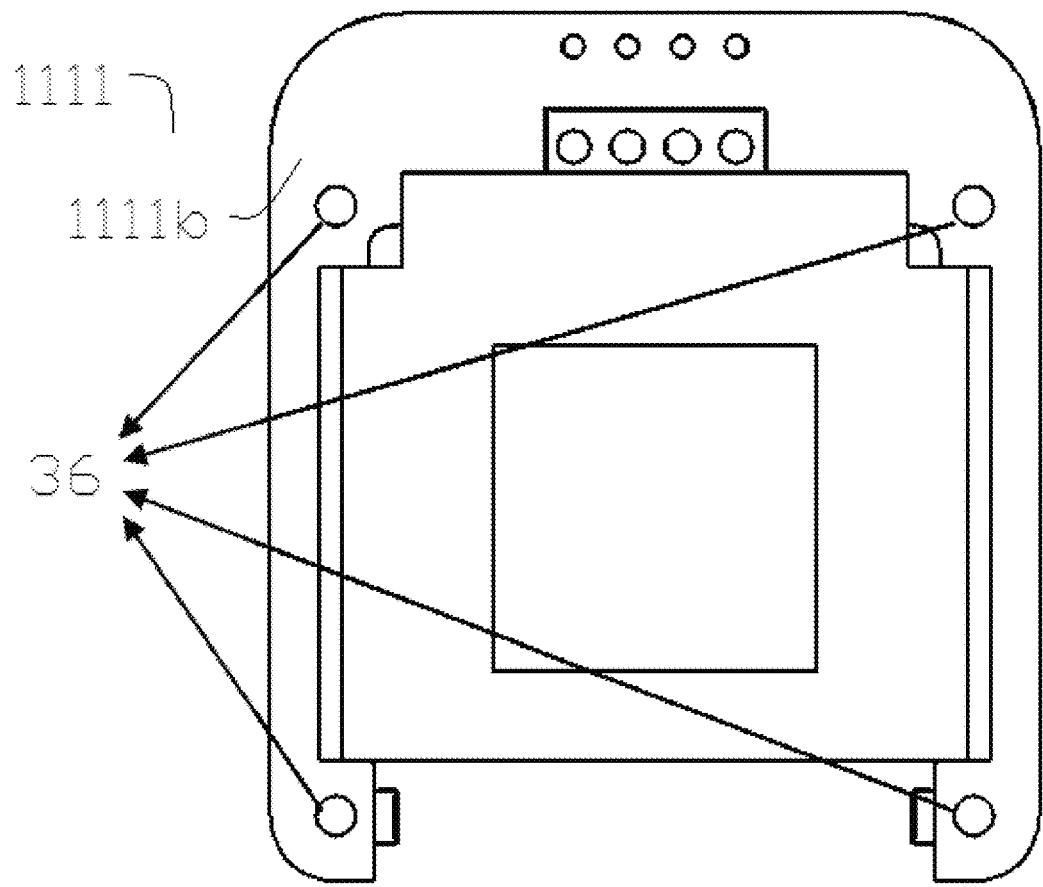
FIG. 6B is a back structural view of an objective table according to at least one embodiment of the present disclosure.

In some embodiments of the disclosure, FIG. 6B is a back structural view of an objective table according to at least one embodiment of the present disclosure. As shown in FIG. 6B, four through holes 36 penetrating from the back surface 1111b to the bearing surface 1111a are disposed on the objective table 1111 for fixedly connecting the objective table 1111 to the support 1113 by fasteners (e.g., screws or bolts). Optionally, the objective table 1111 and the support 1113 may be connected by four compression springs to apply elastic urging forces toward the objective table 1111 and the support 1113. By means of the elastic force of the compression springs, a distance between the objective table 1111 and the support 1113 may be adjusted by tightening or loosening the fasteners, thereby adjusting the levelness of the objective table 1111. Optionally, the four compression springs may be sleeved on the fasteners. Of course, in practical applications, the levelness of the objective table 1111 may also be adjusted by providing other leveling structures, which is not limited in the embodiments of the present disclosure.

Optionally, the objective table 1111 may further include a level meter to detect whether the objective table 1111 is level. The level meter may be adhered to the objective table 1111 by an adhesive or the like, which is not limited in the embodiments of the present disclosure. The level meter may be, for example, a bubble level, an inductive level, a capacitive level, etc., which is not limited in the embodiments of the present disclosure. By means of the level meter, it is possible to detect whether the objective table 1111 is level, and the levelness of the objective table 1111 may be adjusted based on the detection result using the leveling structure, thus the leveling accuracy is increased. In such way, the detection chip 1 (carried by the loading plate body 21) carried on the objective table 1111 is kept level, which facilitates the optical sensor 131 to receive light from the detection chip 1.

As shown in FIG. 6A, the objective table 1111 may have a hollow area 34, such that in a case where the loading plate body 21 is placed on the objective table 1111, the contact surface of the loading plate body 21 and the objective table 1111 is at least partially exposed, for example, is partially exposed to the cooler 122 of the temperature control section 120. Optionally, as shown in FIG. 2B, since the receiving groove 25 on the loading plate body 21 is open on the second plate surface 2b, the detection chip 1 carried by the loading plate body 21 can be exposed to the cooler 122 of the temperature control section 120, thereby improving the cooling efficiency of the detection chip 1. As circumstance requires, the hollow area 34 may be of any suitable shape, such as a circle, a triangle, a rectangle, a pentagon, a hexagon, or other irregular shapes. For another example, the hollow area 34 may have one or a plurality of openings, which is not limited in the embodiments of the present disclosure. The projection of the loading plate body 21 on the plane where the hollow area 34 is located is larger than the size of the hollow area 34, so that the loading plate body 21 will not separate from the objective table 1111 through the hollow area 34.

Figure 6C:
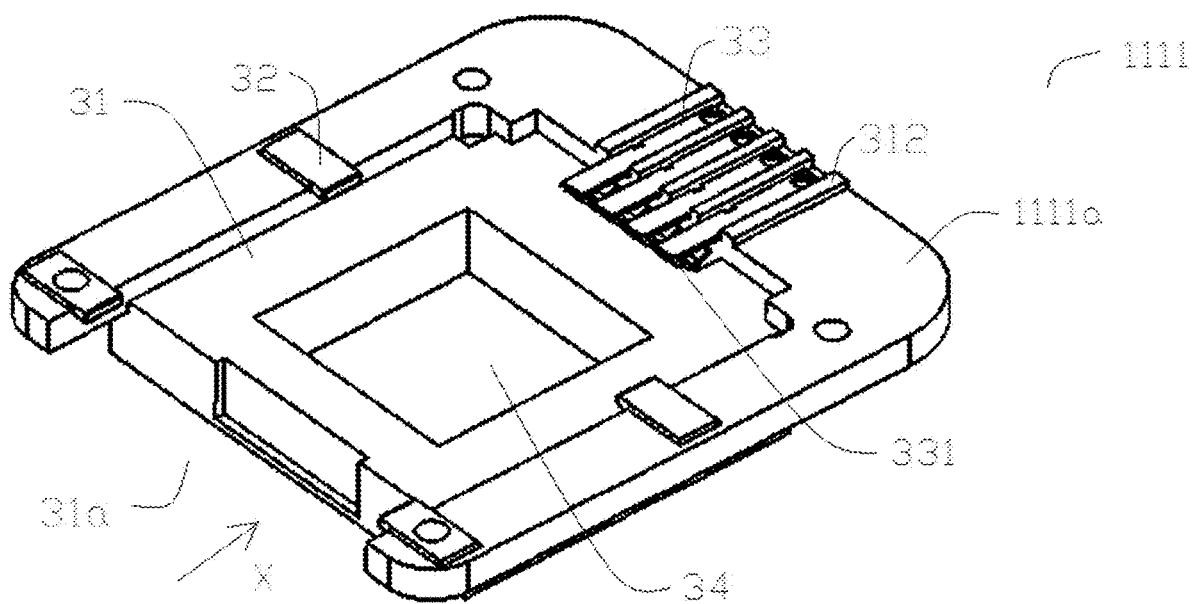
FIG. 6C is a perspective structural view of an objective table according to at least one embodiment of the present disclosure.
Figure 6D:
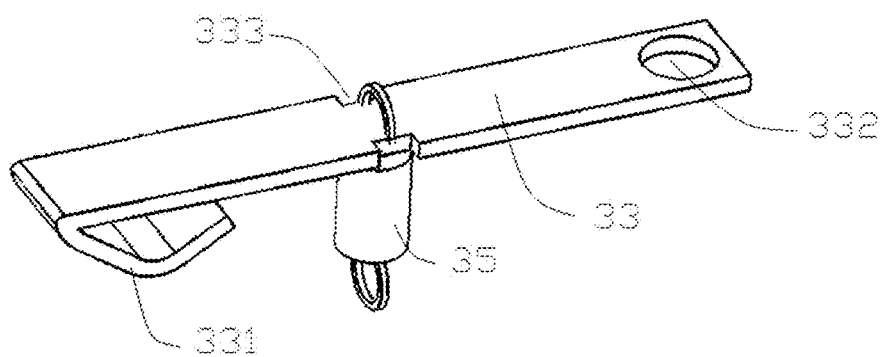
FIG. 6D is a structural view of a contact electrode and a spring according to at least one embodiment of the present disclosure.
Figure 6E:
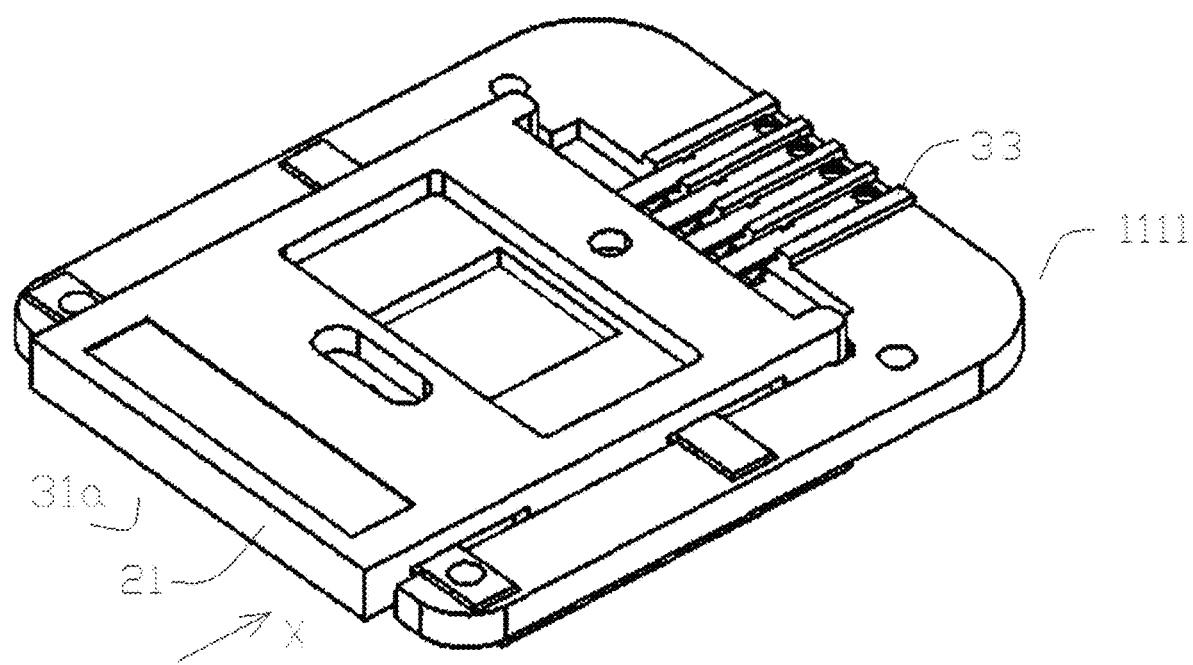
FIG. 6E is a structural view of an objective table bearing a loading plate body according to at least one embodiment of the present disclosure.

In some embodiments of the present disclosure, as shown in FIG. 6D, the heater 121 may include at least one contact electrode 33, and the contact electrode 33 may be formed of, for example, a high temperature resistant metal material. The at least one contact electrode 33 is configured to, in use, be in electrical contact with the at least one heating electrode 11 of the detection chip 1 in a one-to-one correspondence. The heater 121 is further configured to apply an electric signal to the heating electrode 11 of the detection chip 1 through the contact electrode 33, so that the heating electrode 11 heats the detection chip 1.

In some embodiments of the present disclosure, as shown in FIG. 6C, the contact electrode 33 is fixed on the bearing surface 1111a of the objective table 1111 at a side opposite to the mounting groove opening 31a. One end of the contact electrode 33 protrudes relative to a side surface of the mounting groove 31 in a direction opposite to the direction X, i.e., the contact electrode 33 extends from the side of the mounting groove 31 to an interior of the mounting groove 31, so as to, in use, be in electrical contact with the exposed heating electrode 11 of the detection chip 1, and thus apply an electrical signal (e.g., a direct current voltage or an alternating current voltage) to the heating electrode 11 of the detection chip 1. When the detection chip 1 is placed on the objective table 1111, the contact electrode 33 electrically contacts the heating electrode 11 of the detection chip 1, so that an electrical signal can be transmitted. The contact electrode 33 may be electrically connected to a power source or a controller through a wire passing through the objective table 1111 to receive a control signal.

Optionally, a contact portion 331 is disposed on the contact electrode 33 to be in electrical contact with the heating electrode 11. The contact portion 331 protrudes relative to a surface of the contact electrode 33 opposite to the heating electrode 11 toward a direction approaching the heating electrode 11. For example, as shown in FIG. 6D, the contact portion 331 is a protrusion formed by bending one end of the contact electrode 33, and the protrusion preferably forms an acute angle with the contact electrode 33, so as to facilitate insertion of the heating electrode 11 of the detection chip 1 into an inner side of the contact electrode 33. By arranging the contact portion 331 to protrude relative to a surface of the contact electrode 33 opposite to the heating electrode 11, it is possible that, after the loading plate body 21 is placed on the objective table 1111, the contact electrode 33 generates elastic deformation to some extent under extrusion of the loading plate body 21, so that the contact electrode 33 is kept in close contact with the heating electrode 11 to achieve good electrical contact. Also, as shown in FIG. 6D, the heater 121 further includes an elastic piece 35, which is respectively connected to the contact electrode 33 and the objective table 1111, to apply a pulling force to the contact electrode 33 toward the bearing surface 1111a of the objective table 1111. By means of the elastic piece 35, not only an elastic connection between the contact electrode 33 and the objective table 1111 can be achieved, but also the contact electrode 33 can be reset when the loading plate body 21 is moved out of the mounting groove 31. Optionally, the elastic piece 35 is a spring, such as an extension spring. Further, a limiting groove 333 may be disposed on the contact electrode 33 to limit the position of the elastic piece 35 on the contact electrode 33.

Further, optionally, as shown in FIG. 6C, an electrode slot 312 is disposed on the bearing surface 1111a of the objective table 1111, the contact electrode 33 is inserted into the electrode slot 312, and the contact electrode 33 and the objective table 1111 are fixedly connected by a fastener. For example, as shown in FIG. 6D, a mounting hole 332 may be provided at an end of the contact electrode 33 far from the contact portion 331, and fixedly connected to the objective table 1111 by a fastener (e.g., a screw or a bolt). Optionally, as shown in FIG. 6A, limiting steps 311 are further disposed at two corners of a side surface of the mounting groove 31 opposite to the mounting groove opening 31a, so as to limit the position of the loading plate body 21 in the mounting groove 31 while reserving a certain contact space for the heating electrode 11 of the detection chip 1 carried by the loading plate body 21 and the contact electrode 33.

In other embodiments, the detection chip 1 may have no heating electrode, and the heater 121 may be configured to supply infrared rays or air flow for heating to the detection chip 1 to heat the detection chip 1. For example, the heater 121 may be an infrared heater or an air heater (e.g., heating air by resistance and driving heated air flow by a fan), etc., which is not limited in the embodiments of the present disclosure.

The movable platform 1112 is configured to be operably connected to the driver 112 to move under drive of the driver 112. The driver 112 may be, for example, a motor. The movable platform 1112 is connected to, for example, a driving end of the motor. For example, as shown in FIGS. 5A and 5B, the driver 112 may be a rotary motor, a driving end of which is connected to a lead screw S so that the lead screw S can be rotated. The movable platform 1112 is connected to the lead screw S through a nut threadedly engaged with the lead screw S, so that rotation of the lead screw S can be converted into horizontal movement, and the movable platform 1112 can move under the drive of the driver 112. In addition, a guide rod G parallel to the lead screw S may be further provided. The movable platform 1112 is movably connected to the guide rod G. The guide rod G functions to restrain the movable platform 1112. It should be understood that the number of the guide rods G and that of the lead screws S shown in FIGS. 5A and 5B are exemplary, and are not limited in the embodiments of the present disclosure. For example, the driver 112 may be a linear motor, and a mover of the linear motor may be connected to the movable platform 1112 to drive the movable platform 1112 to move. It is not limited in the embodiments of the present disclosure how the driver 112 drives the movable platform 1112, and for example, a rack and pinion combination may be adopted to convert rotational movement into horizontal movement.

The movable platform 1112 may be formed of any rigid material, such as metal, plastic, ceramic, rubber, resin, and the like, which is not limited in the embodiments of the present disclosure. Further, it should be understood that the shape of the movable platform 1112 shown in FIGS. 5A and 5B is also merely exemplary. The movable platform 1112 may have any suitable shape depending on practical requirements.

The support 1113 is configured to connect the objective table 1111 and the movable platform 1112, such that the objective table 1111 may be driven along with the movable platform 1112.

As shown in the dashed border in FIG. 5A, the support 1113 may include a first portion 1113A and a second portion 1113B. The first portion 1113A is configured to, in use, bear an objective table 1111. The second portion 1113B is configured to, in use, be connected to the movable platform 1112. The first portion 1113A extends in a first direction, the second portion 1113B extends in a second direction, and the first direction is perpendicular to the second direction. The support 1113 is formed into an L-shape or a T-shape to decrease the dimension in a single direction, which contributes to reduction of the overall volume of the analysis device.

The first portion 1113A of the support 1113 may be connected to the objective table 1111 by, for example, springs or the like, for example, four springs corresponding to four corners of the objective table 1111, so that the horizontal state of the objective table 1111 can be adjusted by adjusting the respective springs.

The second portion 1113B of the support 1113 may be detachably or fixedly connected to the movable platform 1112 by, for example, screws or the like, to allow the movable platform 1112 to drive the support 1113 to move along. Alternatively, the second portion 1113B may be integrally formed with the movable platform 1112.

The support 1113 may be formed of any rigid material, such as metal, plastic, ceramic, rubber, resin, etc., which is not limited in the embodiments of the present disclosure. Further, it should be understood that the shape of the support 1113 shown in FIGS. 5A and 5B is also merely exemplary, and the support 1113 may be of any suitable shape depending on practical requirements.

Figure 7A:
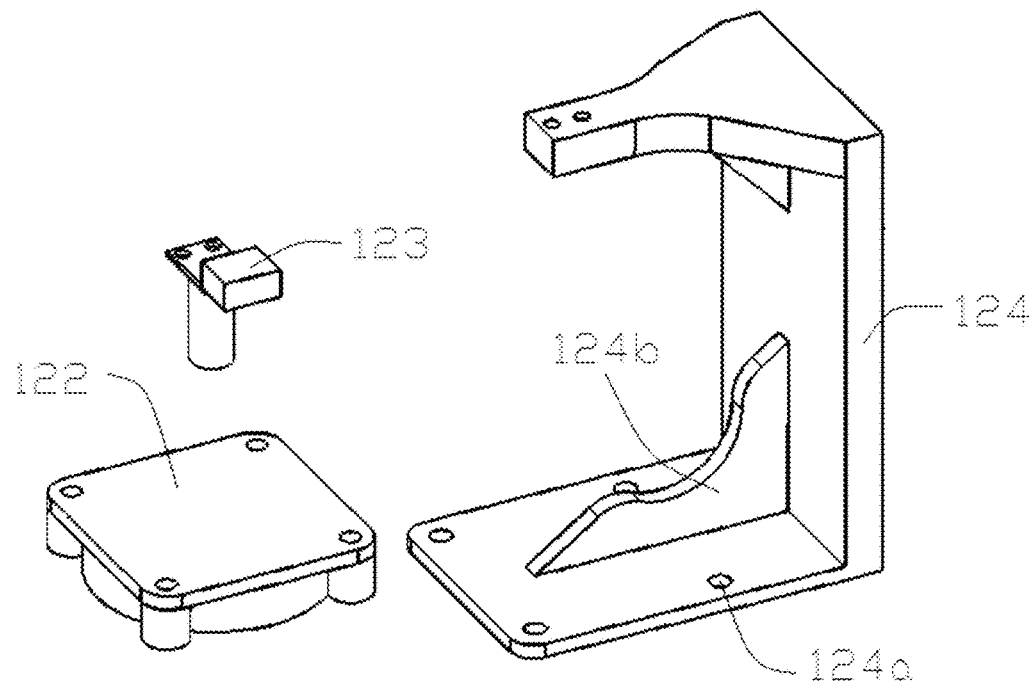
FIG. 7A is a schematic structural view of a temperature control section in an exploded state according to at least one embodiment of the present disclosure.
Figure 7B:
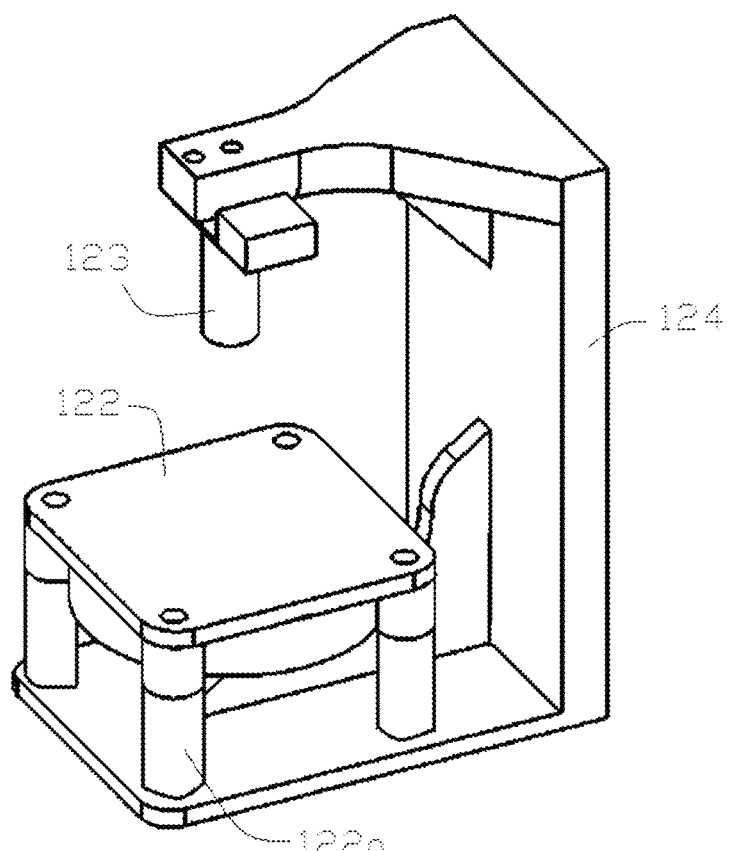
FIG. 7B is a structural view of a temperature control section in an assembled state according to at least one embodiment of the present disclosure.

FIG. 7A is a schematic structural view of a temperature control section in an exploded state according to at least one embodiment of the present disclosure. FIG. 7B is a structural view of a temperature control section in an assembled state according to at least one embodiment of the present disclosure. As shown in FIGS. 7A and 7B, the temperature control section 120 may include, for example, a temperature sensor 123. The temperature sensor 123 is configured to detect temperature of the detection chip 1. The temperature sensor 123 may be a conventional temperature sensor, which will not be described in the embodiment of the present disclosure. For example, the temperature sensor 123 may include an infrared temperature sensor or a thermocouple temperature sensor. It should be understood that, in some embodiments of the present disclosure, if the detection chip 1 includes a temperature sensor, the temperature sensor 123 needs no longer to be disposed in the analysis device.

As shown in FIG. 7B, the temperature sensor 123 and the cooler 122 are configured to be spaced from each other to allow the detection chip 1 to be sandwiched between the temperature sensor 123 and the cooler 122. As shown in FIGS. 7A and 7B, the temperature control section 120 may further include a temperature control stand 124, and the temperature sensor 123 and the cooler 122 are connected to the temperature control stand 124 to be spaced apart from each other. It should be understood that the locations of the temperature sensor 123 and the cooler 122 in FIGS. 7A and 7B are merely exemplary, which are not limited in the embodiments of the present disclosure. For example, in other embodiments, the temperature sensor 123 in use may be located above or below the detection chip 1, while the cooler 122 in use may be located on a side portion of the detection chip 1.

For example, the cooler 122 may include, but is not limited to, a fan or a semiconductor chilling plate, and the specific type of cooler 122 is not limited in the embodiments of the present disclosure. As shown in FIG. 7B, the cooler 122 may be exemplified by a fan having a substantially circular outline and fixed to the temperature control stand 124 by four mounting posts 122a provided at four corners. Specifically, as shown in FIG. 7A, four through holes 124a are provided on a base of the temperature control stand 124 to allow the four mounting posts 122a to be mounted on the base of the temperature control stand 124 in a one-to-one correspondence by screws.

As shown in FIGS. 7A and 7B, the temperature control stand 124 is composed of a bottom plate, and a vertical plate and a horizontal plate provided on the bottom plate. The horizontal plate is disposed relatively above the bottom plate and supported by the vertical plate, the cooler 122 is supported by the bottom plate, and the temperature sensor 123 is disposed on the horizontal plate and located relatively above the cooler 122. In a case where the detection chip 1 in use is located between the temperature sensor 123 and the cooler 122, the temperature sensor 123 can detect the temperature of the detection chip 1; and the cooler 122 can cool down the detection chip 1.

Optionally, as shown in FIG. 7A, a rib plate 124b is further disposed at an intersection between the horizontal plate and the vertical plate to enhance connection stability between the horizontal plate and the vertical plate. The rib plate 124b is perpendicular to the horizontal plate and the vertical plate, and has two side surfaces at a right angle to be attached to the horizontal plate and the vertical plate, respectively. The rib plate 124b further has a wavy side surface to provide a mounting space for the cooler 122.

The temperature control stand 124 may be formed of any rigid material, such as metal, plastic, ceramic, rubber, resin, etc., which is not limited in the embodiments of the present disclosure. Furthermore, it should be understood that the shape of the temperature control stand 124 shown in FIGS. 7A and 7B is also merely exemplary, and the temperature control stand 124 may be of any suitable shape depending on practical requirements.

Figure 8:
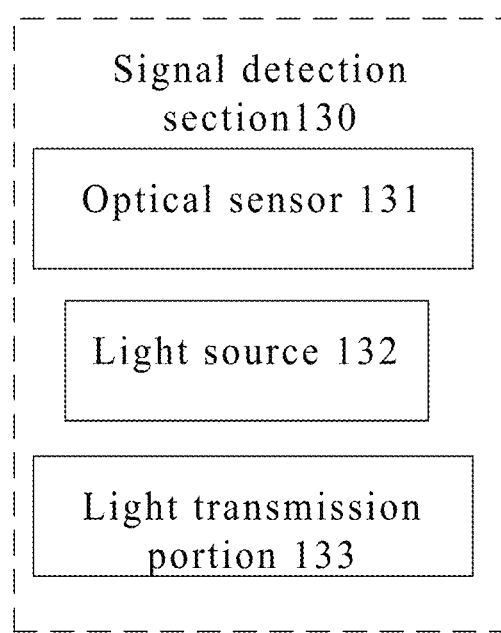
FIG. 8 is a schematic block diagram of a signal detection section according to at least one embodiment of the present disclosure.

FIG. 8 is a schematic block diagram of a signal detection section according to at least one embodiment of the present disclosure. As shown in FIG. 8, in at least one embodiment of the present disclosure, the signal detection section 130 may further include a light source 132 and a light transmission portion 133, in addition to an optical sensor 131.

The optical sensor 131 is, for example, an image sensor configured to capture an image of the detection chip (e.g., a biochip image) for analysis. For example, the optical sensor 131 may include a Charge Coupled Device (CCD) or a Complementary Metal Oxide Semiconductor (CMOS). However, it should be understood that in other embodiments, the optical sensor 131 may also be a photodiode, a photoresistor, an infrared sensor, an ultraviolet sensor, etc., which is not limited in the embodiments of the present disclosure.

The light source 132 may be configured to, in use, provide light to illuminate the detection chip. The light transmission portion 133 may be configured to, in use, transmit light provided by the light source 132 to the detection chip and light emitted by the detection chip to the optical sensor 131.

For example, the light source 132 may be of various types that can emit visible light, infrared light, etc. For example, the light source includes a laser or a fluorescent light source, and the wavelengths of the laser and the fluorescent light source may be selected according to practical requirements, which is not limited in the embodiments of the disclosure.

Figure 9A:
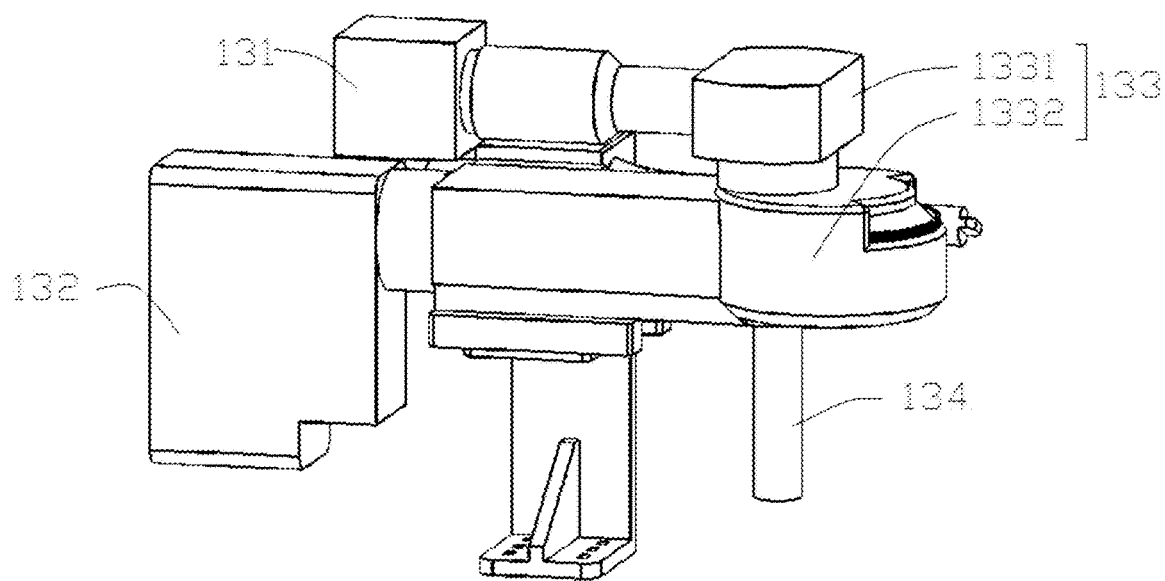
FIG. 9A is a side view of a signal detection section according to at least one embodiment of the present disclosure.
Figure 9B:
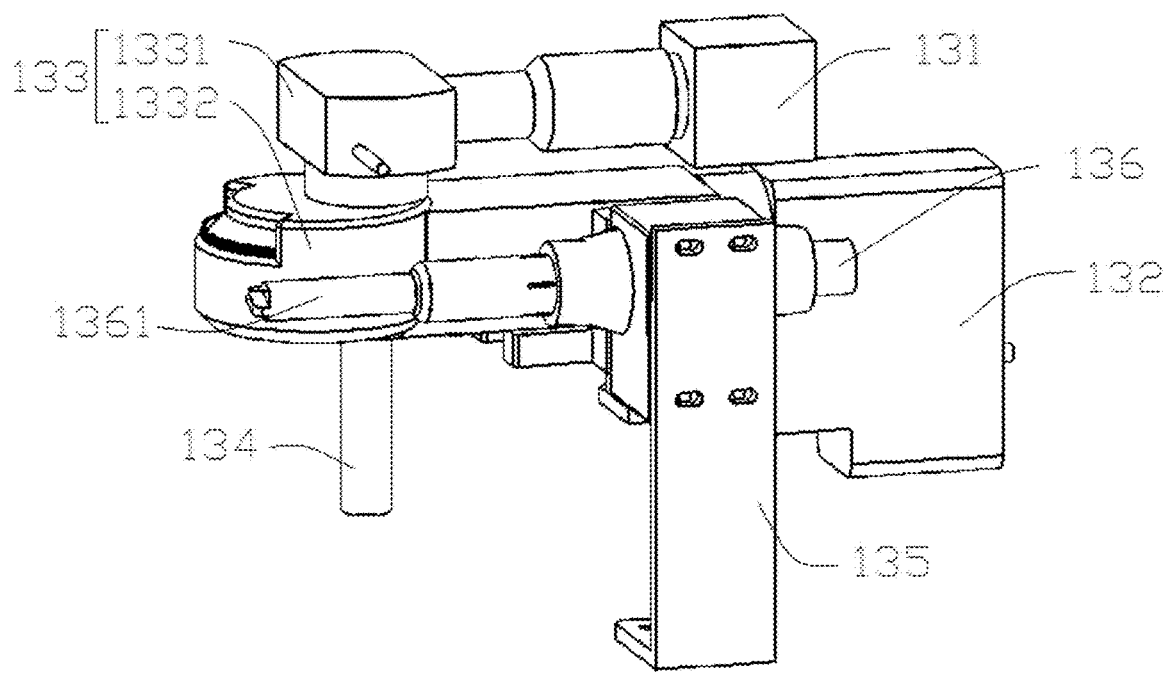
FIG. 9B is another side view of a signal detection section according to at least one embodiment of the present disclosure.

FIG. 9A is a side view of a signal detection section according to at least one embodiment of the present disclosure. FIG. 9B is another side view of a signal detection section according to at least one embodiment of the present disclosure. As shown in FIGS. 9A and 9B, in some embodiments of the present disclosure, the light transmission portion 133 may include a 90° prism system 1331 and a reflective optical path system 1332. The 90° prism system 1331 may be configured to transmit light from the detection chip to the optical sensor 131. The reflective optical path system 1332 may be configured to transmit light from light source 132 to illuminate the detection chip, and the reflective optical path system 1332 may further include a filter on the optical path from the detection chip to the optical sensor 131 to filter light transmitted on the optical path, thus to allow only light of a set wavelength to pass through. Both the 90° prism system 1331 and the reflective optical path system 1332 may be of conventional design in the art, and will not be described in detail herein.

As shown in FIGS. 9A and 9B, in some embodiments, the signal detection section 130 may further include an objective lens 134. The objective lens 134 is configured to collect light from the detection chip. For example, the objective lens 134 may include a lens.

As shown in FIGS. 9A and 9B, in some embodiments, the signal detection section 130 may further include a bracket 135. The bracket 135 is configured to fix and bear at least some of the components of the signal detection section 130, such as the light source 132, the light transmission portion 133, and the like. In some embodiments, a focal length adjustment structure is further disposed on the bracket 135, and the focal length adjustment structure is configured to adjust a distance between the light transmission portion 133 and the detection chip, so that the detection chip is located at a focus of the light transmission portion 133. Also, as shown in FIG. 9B, the focal length adjustment structure has a focal length adjustment knob 136 and a knob extension 1361 connected to the focal length adjustment knob 136, and the knob extension 1361 extends to a side close to the light transmission portion 133 to facilitate manual adjustment. The bracket 135 may be of a conventional design in the art and will not be described in detail in the present disclosure.

In some embodiments, the signal detection section 130 may further include a level meter (not shown in the drawings) to detect whether the signal detection section 130 is level. For example, the level meter may be connected to the light transmission portion 133, the optical sensor 131, the light source 132, and the like. As an example, the level meter may be connected to a 90° prism system 1331. However, it should be understood that embodiments of the present disclosure are not limited thereto. The level meter may be connected to other components of the signal detection section 130 by any suitable means, such as adhesion, magnetic attraction, screwing, etc., which is not limited in the embodiments of the present disclosure. The level meter may be, for example, a bubble level, an inductive level, a capacitive level, etc., which is not limited in the embodiments of the present disclosure. By means of the level meter, for example, light transmitted from the light transmission portion 133 to the detection chip can be perpendicular to the detection chip or light from the detection chip can perpendicularly enter the light transmission portion 133, thereby facilitating subsequent signal processing, for example, a step of angle-correcting an image of the detection chip may be omitted.

Figure 10:
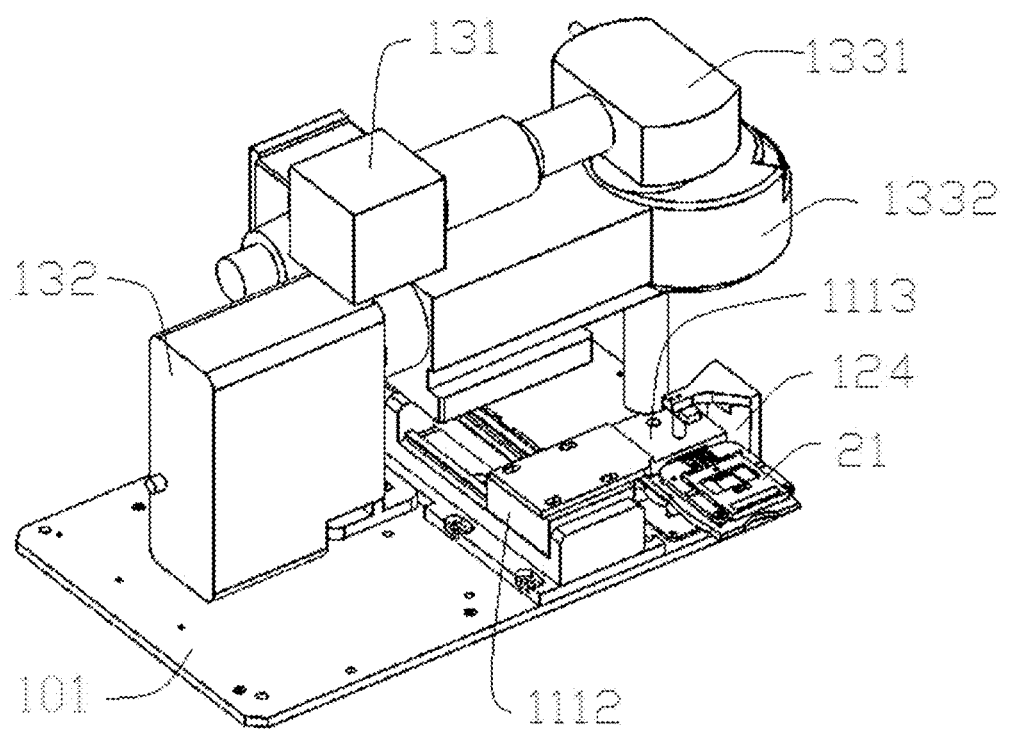
FIG. 10 is an overall internal structural view of an analysis device according to at least one embodiment of the present disclosure.

FIG. 10 is an overall internal structural view of an analysis device according to at least one embodiment of the present disclosure. As shown in FIG. 10, the analysis device may include a base 101, and the transportation section 110, the temperature control section 120, and the signal detection section 130 are all disposed on the base 101 and fixed to the base 101, for example, by screws, clamps, adhesives, or the like. The temperature control section 120 and the signal detection section 130 may be disposed along a movement path of the movable platform 1112 in the transportation section 110, so that the loading plate body 21 borne on the objective table 1111 may be moved by the movement of the movable platform 1112 to the location of the temperature control section 120 for temperature control and to the signal detection section 130 for collecting light from the detection chip.

However, it should be understood that the arrangement shown in FIG. 10 is exemplary, and different arrangements may be adopted according to different structures and shapes of the transportation section 110, the temperature control section 120 and the signal detection section 130, which is not limited in the embodiments of the present disclosure.

In some embodiments of the present disclosure, the analysis device 100 further includes one or a plurality of controllers. The one or plurality of controllers may be configured to perform at least one of the following operations:

signally connecting with the transportation section 110 to control the transportation section 110 to move;

signally connecting with the heater 121 to control the heater 121 to heat the detection chip;

signally connecting with the cooler 122 to control the cooler 122 to cool the detection chip; and signally connecting with the optical sensor 131 to analyze light from the detection chip.

The controller may be implemented, for example, by a Central Processing Unit (CPU), a Digital Signal Processor (DSP), a Single Chip Micyoco (SCM), a Field Programmable Gate Array (FPGA), a Complex Programmable Logic Device (CPLD), an Application Specific Integrated Circuit (ASIC), and the like, which is not limited in the embodiments of the present disclosure.

It should be understood that in some embodiments of the present disclosure, the controller may be implemented as a plurality of sub-controllers that may each perform at least one of the operations described above. The plurality of sub-controllers may be separately provided or integrated in one controller, which is not limited in the embodiments of the present disclosure.

In some embodiments of the present disclosure, the analysis device 100 may further include a communication unit. The communication unit is configured to form a signal connection with a mobile terminal, a server, or the like. The signal connection may be a wired connection or a wireless connection, which is not limited in the embodiments of the present disclosure. Exemplary Wireless connections include Wireless fidelity (Wi-Fi), Bluetooth, Wireless Direct (Wireless Direct), and infrared. Exemplary wired connections include Universal Serial Bus (USB), FireWire (FireWire), Thunderbolt (Thunderbolt), or any connection that requires a physical cable.

Figure 11A:
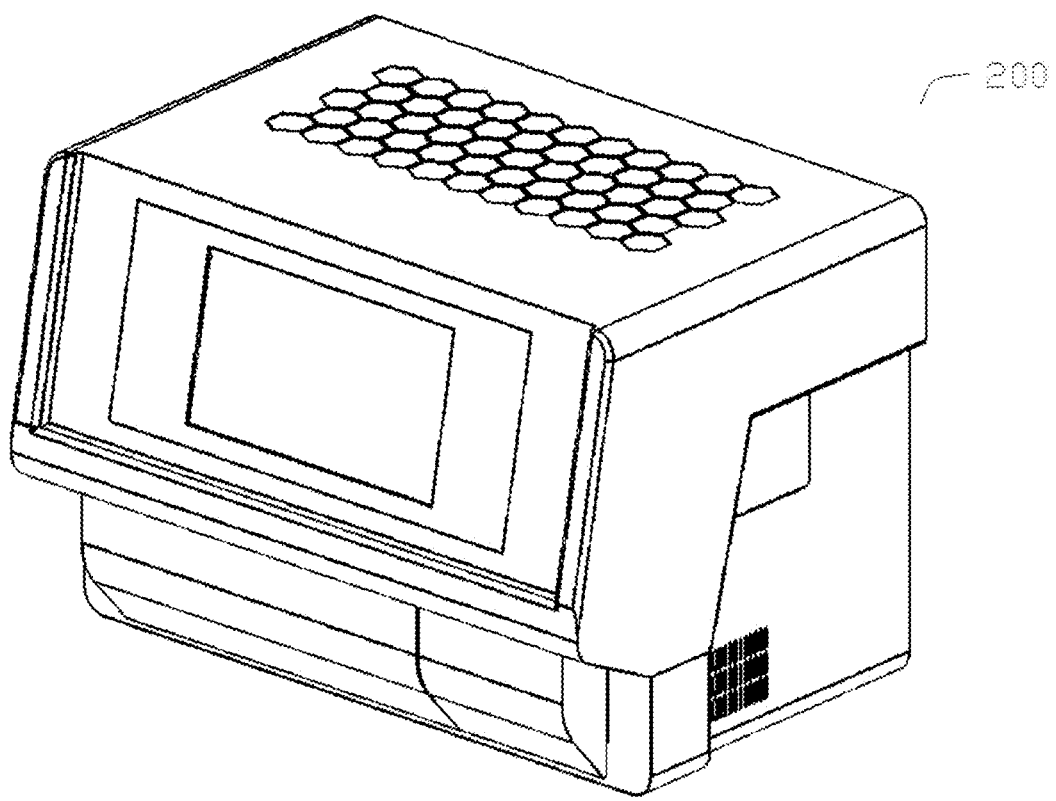
FIG. 11A is an overall external structural view of an analysis device according to at least one embodiment of the present disclosure.
Figure 11B:
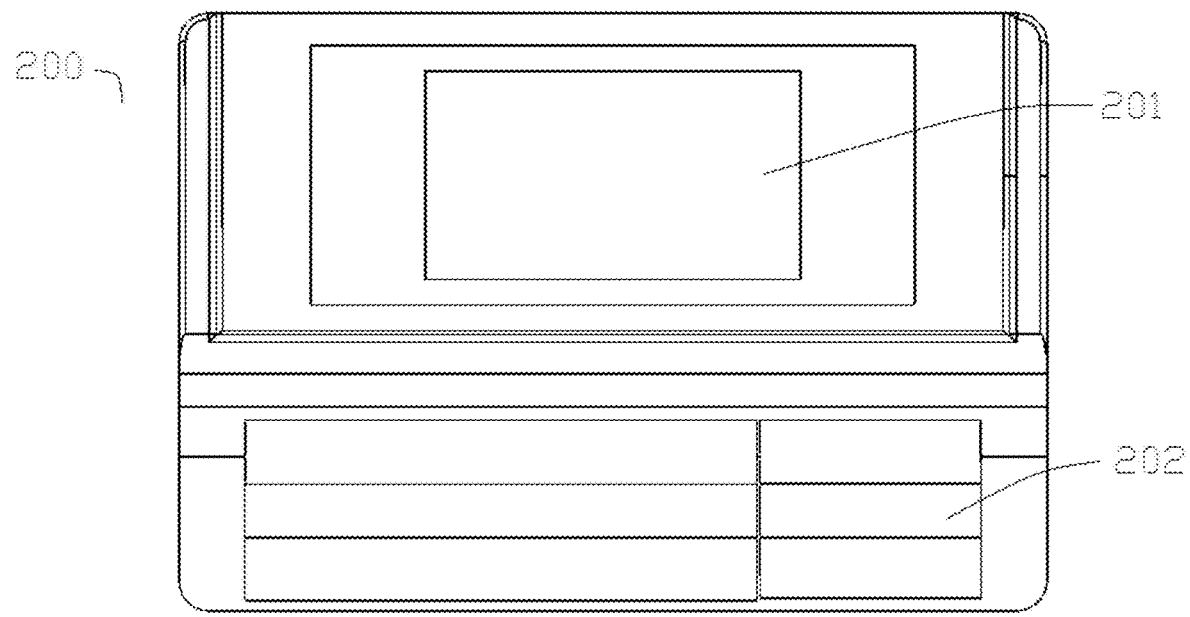
FIG. 11B is an external front view of an analysis device according to at least one embodiment of the present disclosure.

FIGS. 11A to 11G are respectively a perspective view and six side views (except for a top surface) of a housing 200 of an analysis device according to at least one embodiment of the present disclosure. As shown in FIG. 11B, an analysis device according to at least one embodiment of the present disclosure may further include a display screen 201. The display screen 201 is disposed on the front surface of the housing 200 and configured to display. The display screen 201 may be, for example, a liquid crystal display, an Organic Light Emitting Diode (OLED) display, a quantum dot light emitting diode (QLED) display, a micro light emitting diode display, an electronic ink display, an electronic paper display, or the like, which is not limited in the embodiments of the present disclosure. For example, the display screen 201 may be a touch display screen to receive input from a user. However, it should be understood that, in some embodiments, the analysis device may not include the display screen 201, but be connected to a separately provided display screen or output data, such as analysis results, in the form of a digital file or a physical file, which is not limited in the embodiments of the present disclosure.

Optionally, the front surface of the housing 200 may further be provided with a loading valve 202 which, when opened, allows the objective table 1111 to protrude from the loading valve to receive the loading plate body 21.

Figure 11C:
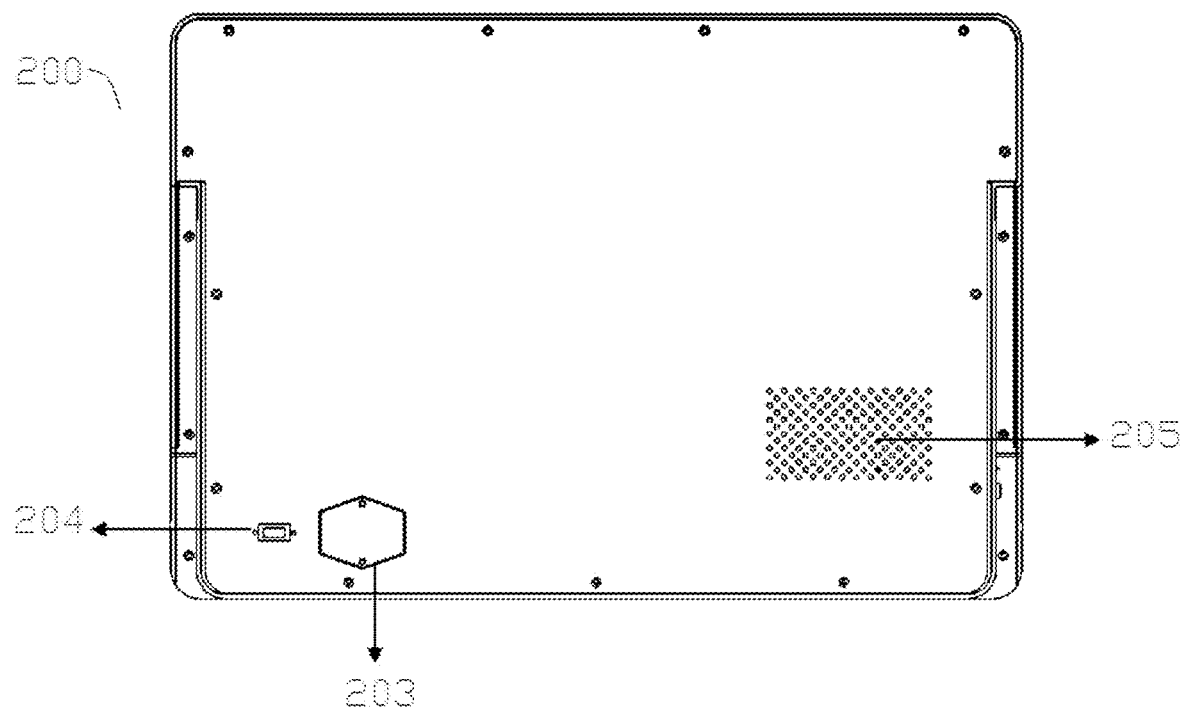
FIG. 11C is an external back view of an analysis device according to at least one embodiment of the present disclosure.

As shown in FIG. 11C, the analysis device according to at least one embodiment of the present disclosure may further include a power interface 203. The power interface 203 is, for example, disposed on the back surface of the housing 200, and the analysis device is connected to a power source through the power interface 203 to obtain power. However, it should be understood that, in some embodiments, the analysis device may not have the power interface 203, and instead, have a built-in primary battery or secondary battery, or a built-in solar battery, which is not limited in the embodiments of the present disclosure.

As shown in FIG. 11C, the analysis device according to at least one embodiment of the present disclosure may further include a data transmission interface 204. The data transmission interface 204 is disposed, for example, on the back surface of the housing 200, and is configured to output data such as an analysis result of the analysis device to an external device or transmit data from an external device to the analysis device. The data transmission interface 204 may be, for example, a Universal Serial Bus (USB) interface, a Serial Advanced Technology Attachment (SATA) interface, or the like. In at least one embodiment, the data transmission interface and the power interface may be combined into one interface, such as a USB interface, for transmitting both data and power. The analysis device according to at least one embodiment of the present disclosure may further include a key. The key is configured to obtain an input instruction of a user, and may be, for example, a mechanical key, an optical key, and the like, which is not limited in the embodiments of the present disclosure.

Figure 11D:
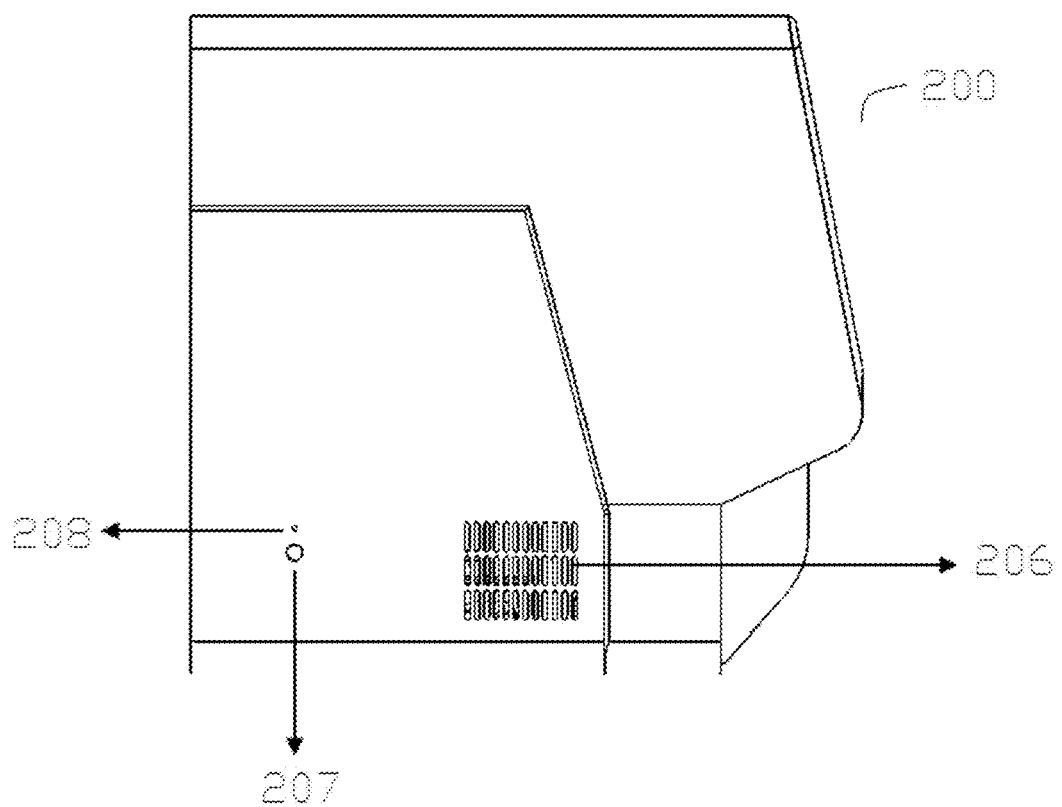
FIG. 11D is an external side view of an analysis device according to at least one embodiment of the present disclosure.

As shown in FIG. 11D, the analysis device according to at least one embodiment of the present disclosure may further include a power switch 207 and an indicator lamp 208, which are disposed, for example, at one side of the housing 200.

Figure 11E:
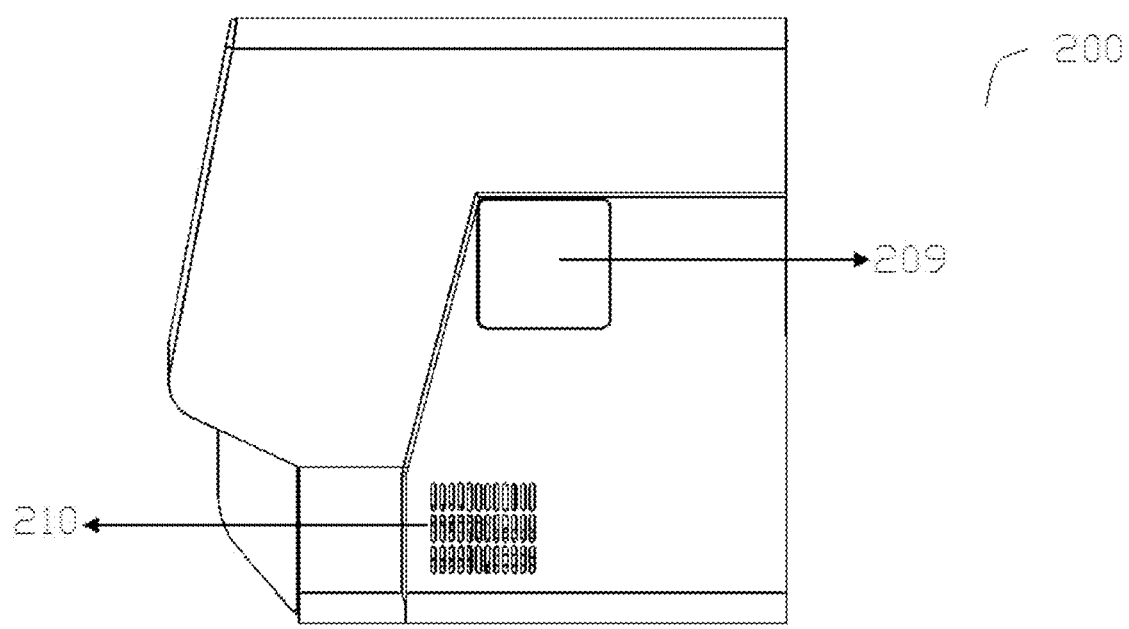
FIG. 11E is another external side view of an analysis device according to at least one embodiment of the present disclosure.
Figure 11F:
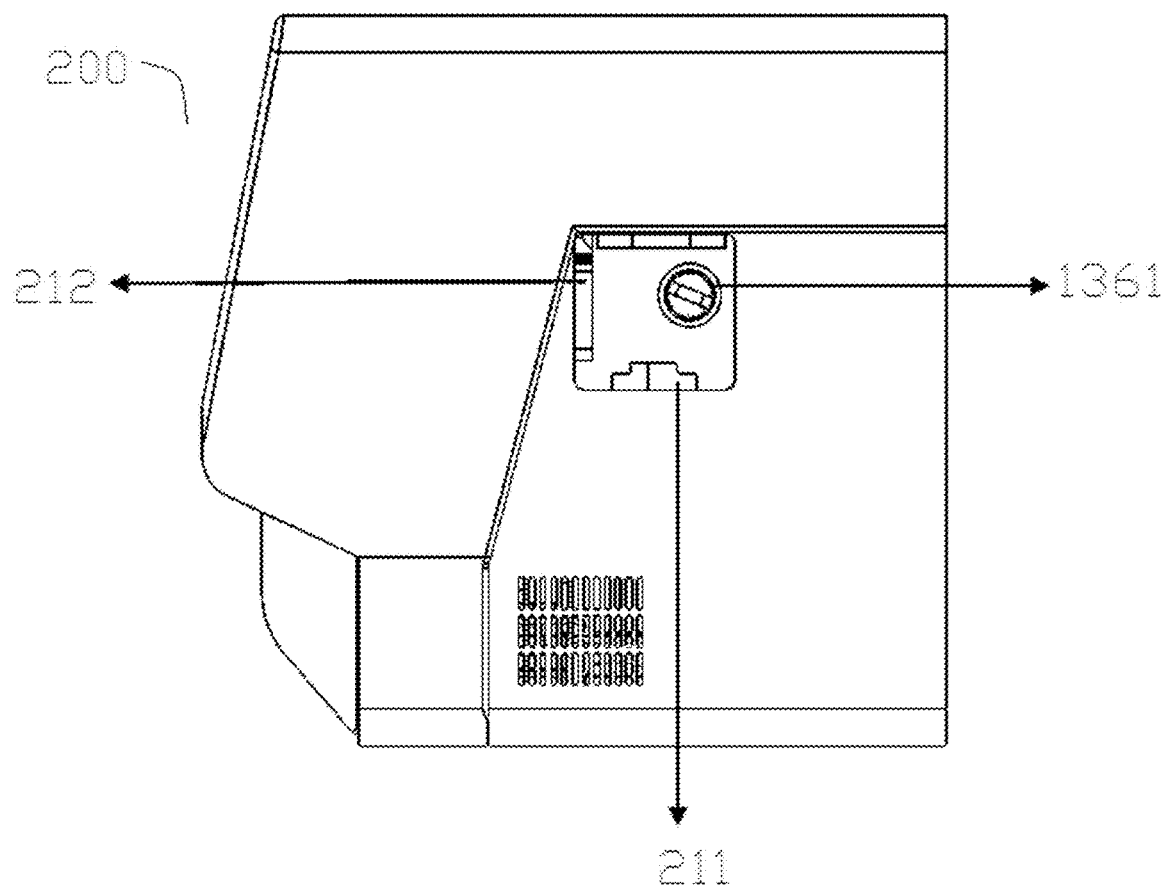
FIG. 11F is another external side view of an analysis device with a control valve being open according to at least one embodiment of the present disclosure.

As shown in FIG. 11E, the analysis device according to at least one embodiment of the present disclosure may further include a control valve 209, which is disposed, for example, at one side of the housing 200 (which may be a different side from the side where the power switch 207 and the indicator lamp 208 described above are located). As shown in FIG. 11F in which the control valve 209 is removed, a magnetic patch 211 is disposed on the inner side of the control valve 209 to fix the control valve 209 by magnetic attraction. Of course, in practical applications, the control valve 209 may be detachably fixed to the housing 200 in other manners, or the control valve 209 may be movably connected to the housing 200 to open or close a control opening. Also, after the control valve 209 is removed, a filter wheel 212 is exposed through the control opening for manual selection of a fluorescent channel. Also, the knob extension 1361 may also be exposed for manual focal length adjustment.

It should be noted that the fluorescent channel may be selected in two operation modes: one is by manual adjustment as described above, the other is by a built-in automation control unit to select the fluorescent channel automatically. Similarly, the focal length adjustment may also have two operation modes: one is to utilize the knob extension 1361 to perform manual adjustment, and the other is to utilize a built-in automation control unit for adjustment of the focal length automatically.

Figure 11G:
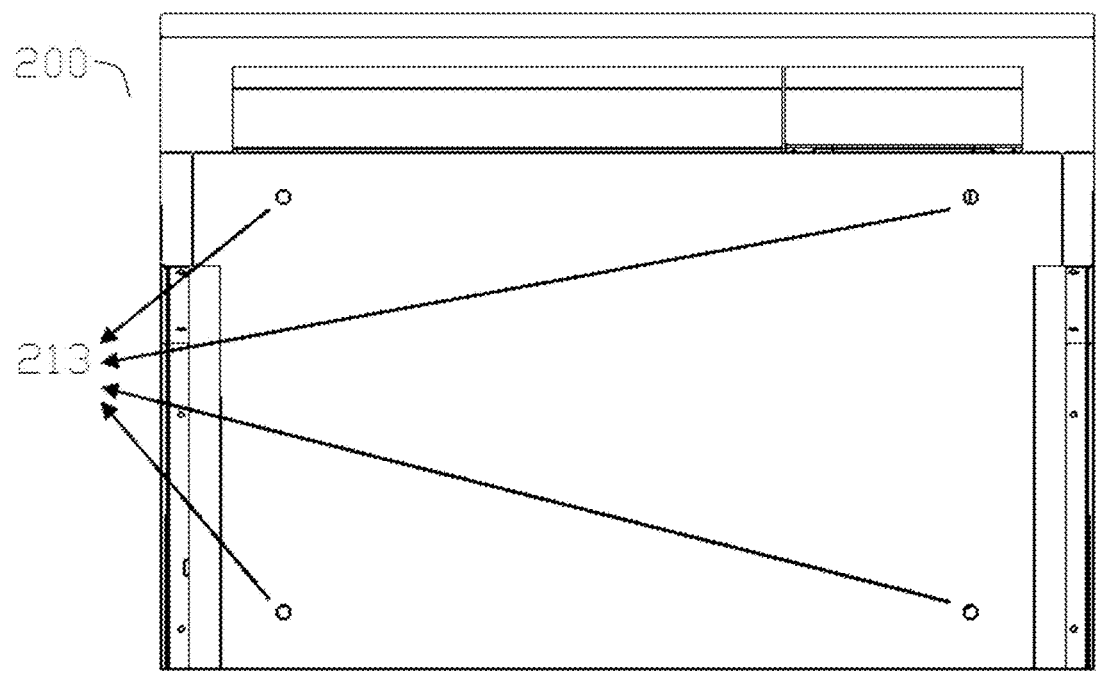
FIG. 11G is an external bottom view of an analysis device according to at least one embodiment of the present disclosure.

As shown in FIG. 11G, the analysis device according to at least one embodiment of the present disclosure may further include four support feet 213 disposed on a bottom surface of the housing 200. Optionally, the four support feet 213 have a levelness adjustment structure (e.g., including screws and elastic pieces) to adjust the levelness of the analysis device as a whole.

As shown in FIGS. 11C, 11D and 11E, the analysis device according to at least one embodiment of the present disclosure may further include heat dissipation openings 205, 206, and 210, which are disposed on the back surface and two sides of the housing 200, respectively, and may be configured to dissipate heat of the controller or the temperature control section 120. These heat dissipation openings may be provided in a dust-free encapsulation to prevent dust from entering the interior of the analysis device.

The analysis device according to at least one embodiment of the present disclosure may further include a touch sensor. The touch sensor is configured to receive and detect a touch operation of a user, and convert a touch operation of the user into an electrical signal for transmission to a controller or other control device, such as a controller or an external server. The touch sensor may be, for example, a capacitive touch sensor, a resistive touch sensor, or the like, which is not limited in the embodiments of the present disclosure. It should be understood that in the case where the display screen 201 is a touch display screen or the analysis device includes other forms of input devices (e.g., keys, microphones, etc.), the analysis device may not include a touch sensor.

Figure 12A:
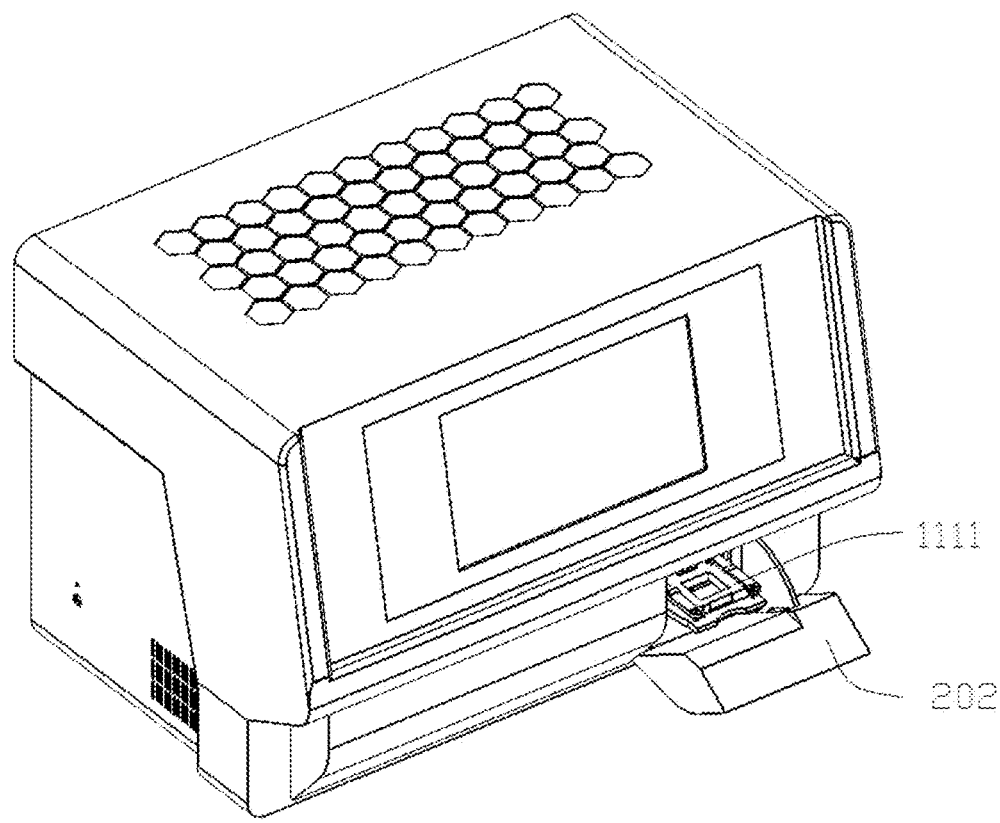
FIG. 12A is a state view of an analysis device with a loading valve being open according to at least one embodiment of the present disclosure.
Figure 12B:
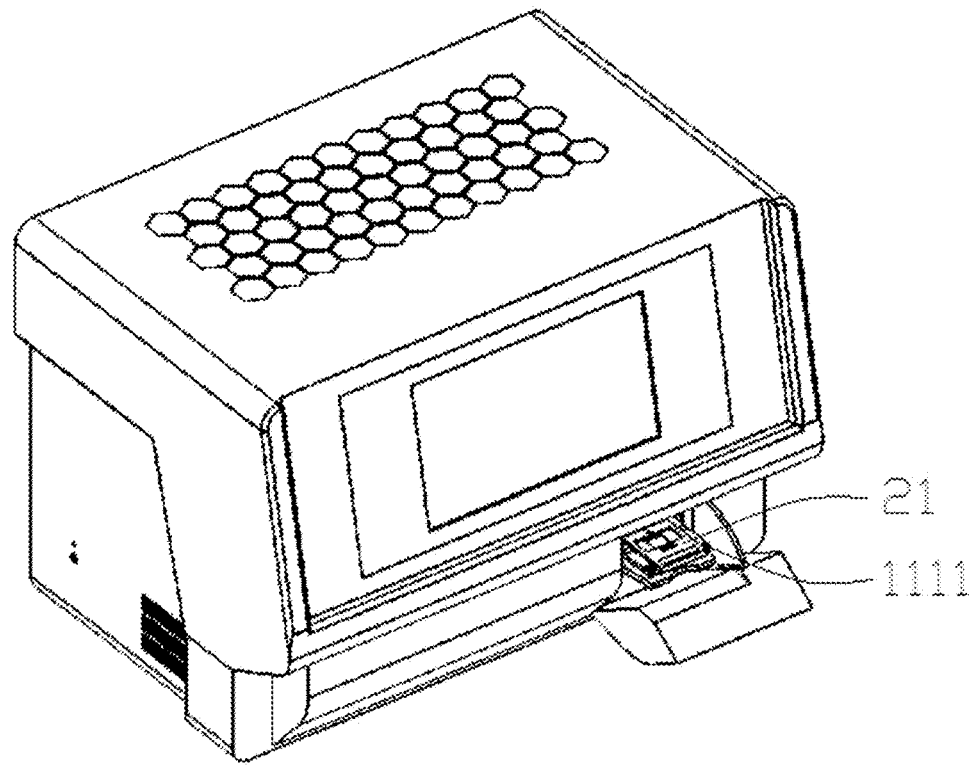
FIG. 12B is a state view of an analysis device with a loading plate body in the first position according to at least one embodiment of the present disclosure.
Figure 12C:
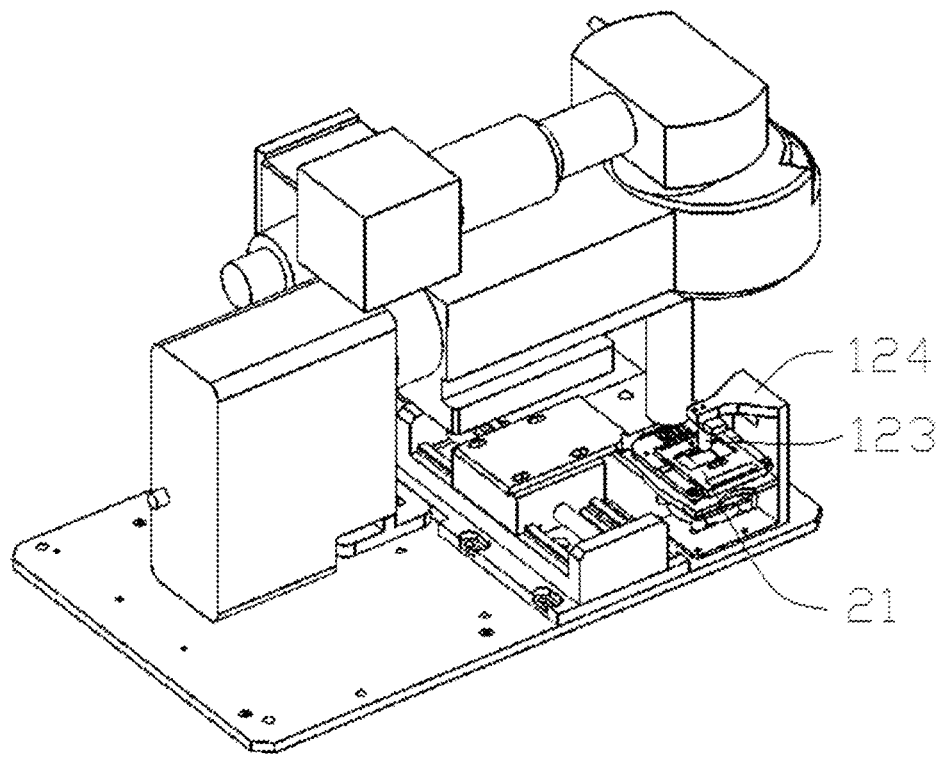
FIG. 12C is a state view of an analysis device with the loading plate body in the second position according to at least one embodiment of the present disclosure.
Figure 12D:
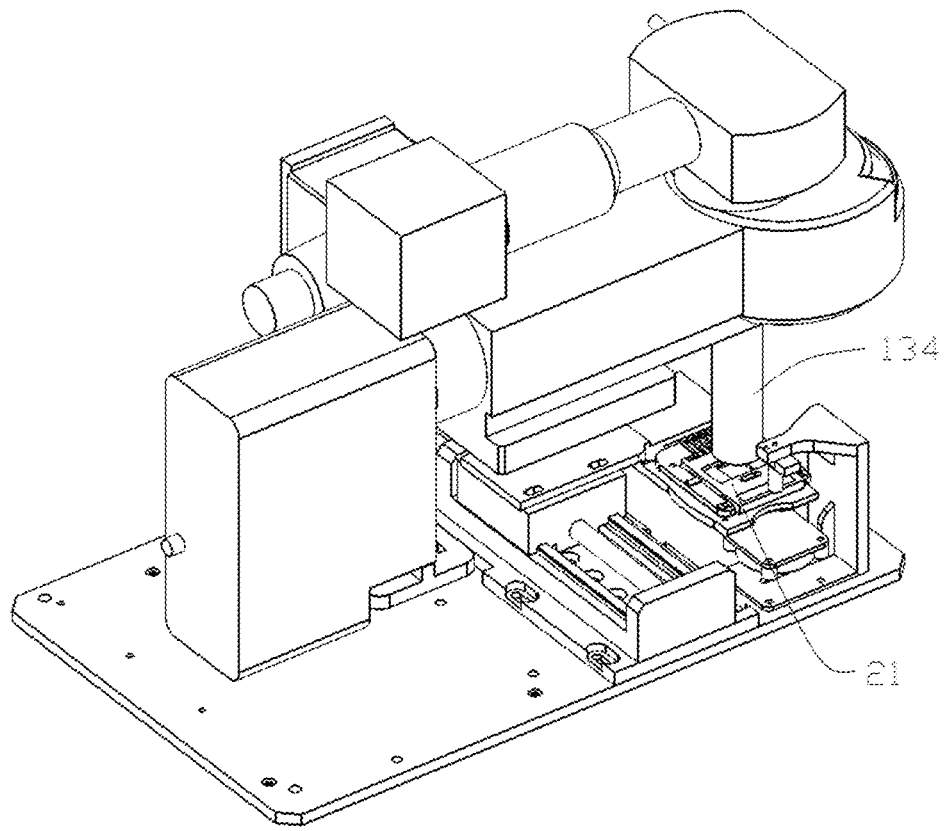
FIG. 12D is a state view of an analysis device with the loading plate body in the third position according to at least one embodiment of the present disclosure.

FIGS. 12A to 12D show state views of an analysis device with the loading plate body 21 being in different positions according to at least one embodiment of the present disclosure. As shown in FIG. 12A, the loading valve 202 of the analysis device according to at least one embodiment of the present disclosure is opened, and the objective table 1111 protrudes from a chip loading port of the analysis device to receive the loading plate body 21. As shown in FIG. 12B, the loading plate body 21 (bearing the detection chip) is in a first position where the loading plate body 21 is received and borne on the objective table 1111. As shown in FIG. 12C, the loading plate body 21 is in the second position, in which case the loading plate body 21 is located between a temperature sensor 123 and a cooler 122 on a thermometric stand 124. The temperature sensor 123 can detect the temperature of the detection chip; the cooler 122 can cool down the detection chip. The second position allows the temperature control section 130 to adjust the temperature of the detection chip. As shown in FIG. 12D, the loading plate body 21 is in a third position, in which case the loading plate body 21 is located below the objective lens 134, so that the objective lens 134 can collect light from the detection chip.

Figure 13:
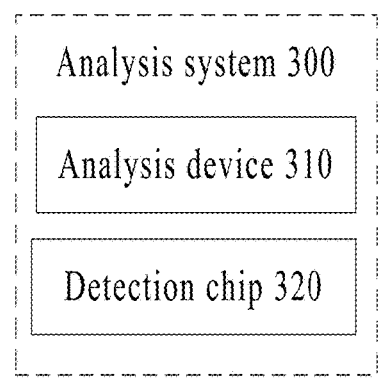
FIG. 13 is a schematic block diagram of an analysis system according to at least one embodiment of the present disclosure.

At least one embodiment of the present disclosure further provides an analysis system. FIG. 13 is a schematic block diagram of an analysis system according to at least one embodiment of the present disclosure. As shown in FIG. 13, an analysis system 300 includes an analysis device 310 and a detection chip 320. For example, the analysis device 310 and the detection chip 320 that is not used may be provided to a user in combination for use by the user. The analysis device 310 may be any of the analysis devices described above. The detection chip 320 may be any of the detection chips described above.

It should be understood that in some embodiments of the present disclosure, the analysis system 300 may also include further components or parts, which is not limited in the embodiments of the present disclosure. For the detailed description and technical effects of the analysis device 310 and the detection chip 320, reference may be made to the above description of the reaction device, and description is not repeated herein.

At least one embodiment of the present disclosure further provides a method of operating an analysis device. The method is applicable to the analysis device according to any embodiment of the present disclosure. The method of operating an analysis device according to at least one embodiment of the present disclosure may include the following step:

step 1, moving a transportation section bearing a loading section (i.e., a loading plate body bearing a detection chip in a chip loading structure) to a temperature control section.

In step 1, the transportation section may be manually moved to the temperature control section. In the case where the transportation section includes a transportation structure that is configured to bear the loading plate body and is at least partially driven and a driver that is configured to be capable of driving the transportation structure, step 1 may include driving, by the driver, the transportation structure bearing the loading plate body, so as to move the loading plate body to the temperature control section.

FIGS. 12A to 12D show state views of an analysis device with the loading plate body 21 in different positions according to at least one embodiment of the present disclosure. As shown in FIG. 12A, a loading valve 202 of the analysis device according to at least one embodiment of the present disclosure is opened, and the objective table 1111 protrudes from the chip loading port of the analysis device to receive the loading plate body 21. As shown in FIG. 12B, the loading plate body 21 (bearing the detection chip) is in a first position where the loading plate body 21 is received and borne on the objective table 1111. As shown in FIG. 12C, the loading plate body 21 is in the second position, in which case the loading plate body 21 is located between the temperature sensor 123 and the cooler 122 on the thermometric stand 124. The temperature sensor 123 can detect the temperature of the detection chip, and the cooler 122 can cool down the detection chip. The second position allows the temperature control section 130 to adjust the temperature of the detection chip.

The method of operating an analysis device according to at least one embodiment of the present disclosure may further include:

step 2, adjusting the temperature of the detection chip through a heater and a cooler.

In the case where the detection chip has a heating electrode and the heater includes a contact electrode, the step 2 may include applying an electrical signal to the heating electrode of the detection chip through a contact electrode, so that the heating electrode heats the detection chip.

Figure 14:
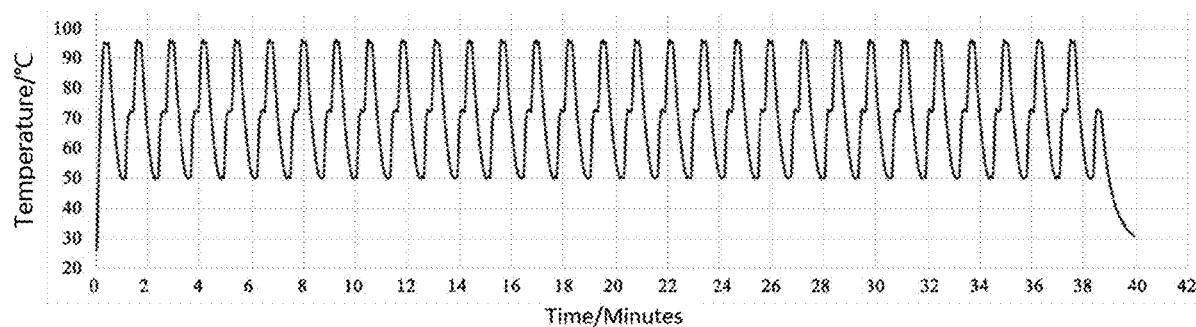
FIG. 14 is a graph of temperature change of a temperature control cycle according to at least one embodiment of the present disclosure.

In some embodiments, the step 2 further includes: maintaining the detection chip at at least two temperatures recurrently by a heater and a cooler. For example, the detection chip is heated by a heater and cooled by a cooler. A plurality of temperature control cycles, for example, 30 temperature control cycles, are performed on the detection chip, so that the detection chip performs PCR thermal cycle amplification. Each temperature control cycle includes: maintaining the detection chip at 95° C. for 10 seconds; maintaining the detection chip at 50° C. for 10 seconds; maintaining the detection chip at 72° C. for 10 seconds. It should be understood that the temperature control cycle described above is merely exemplary, which is not limited in the embodiments of the present disclosure. FIG. 14 is a graph of temperature change of a temperature control cycle according to at least one embodiment of the present disclosure. In FIG. 14, the horizontal axis represents time in minutes, and the vertical axis represents temperature in degrees celsius.

The method of operating the analysis device according to at least one embodiment of the present disclosure may further include:

step 3, moving the transportation section to a signal detection section, and obtaining light from the detection chip through an optical sensor.

In step 3, the transportation section may be manually moved to the signal detection section. In the case where the transportation section includes a transportation structure, which is configured to bear the loading plate body and is at least partially driven, and a driver, which is configured to be capable of driving the transportation structure, step 3 may include driving the transportation section through the driver to move the detection chip to the signal detection section.

As shown in FIG. 12D, the loading plate body 21 is in a third position. At that time, the loading plate body 21 is located below the objective lens 134, so that the objective lens 134 can collect light from the detection chip.

The step 3 may further include: illuminating the detection chip with light, and receiving, through an optical sensor, light emitted from the detection chip as light from the detection chip.

In the case where the optical sensor includes an image sensor, the step 3 may include obtaining an image of the detection chip through an image sensor. Further, in the case where the signal detection section further includes a light source and a light transmission portion, the step 3 may include: providing light through a light source; transmitting light provided by the light source through the light transmission portion to illuminate the detection chip; and transmitting light emitted from the detection chip as light from the detection chip through the light transmitting portion to the optical sensor (or an image sensor included in the optical sensor).

The method of operating an analysis device according to at least one embodiment of the present disclosure may further include:

step 4, analyzing the light from the detection chip to obtain an analysis result.

It should be understood that one or a plurality of steps and at least part of sub-steps of the method described above may be executed by software or firmware, for example, by a mobile terminal, a server, etc. in signal connection with the analysis device, which is not limited in the embodiments of the present disclosure.

In some embodiments, in the case where obtaining light from the detection chip through an optical sensor includes obtaining an optical image of the detection chip through an image sensor, taking the optical image as a biochip image as an example, the step 4 may adopt the following biochip image analysis method to identify a fluorescent image of a matrix type biochip of high flux and low signal to noise ratio, so as to realize chamber positioning, and automatic analysis of sample negative and positive determination.

In some embodiments, a method of analyzing a biochip image includes: step 41, step 42, and step 43;

In step 41, obtaining a biochip image and performing preprocessing to obtain a preprocessed image;

In step 42, performing angle deflection correction on the preprocessed image to obtain a deflection corrected image; and In step 43, performing enhancement processing on the deflection corrected image and identifying positivity and negativity of an area of interest in the preprocessed image according to an enhanced image.

In some embodiments, the step 41 includes: step 411 and step 412;

In step 411, acquiring a raw image, a camera internal parameter matrix and a distortion coefficient; and In step 412, correcting the raw image according to the camera internal parameter matrix and the distortion coefficient to obtain a biochip image.

It can be understood that the distortion generated in the raw image captured by a camera can be corrected by acquiring the camera internal parameter matrix and the distortion coefficient, so that the corrected biochip image can more truly show the characteristics of the biochip. In such way, effectiveness and accuracy of the biochip analysis can be ensured.

In some examples, the biochip may have a quadrilateral shape, and a plurality of reaction chambers are disposed in arrays on the biochip. It should be noted that in the embodiment of the present application, description is made by taking an area where the reaction chambers are located in the biochip image as the area of interest.

In some embodiments, the method of analyzing a biochip image includes: calibrating a camera for shooting using a calibration plate and a traditional calibration method to obtain a camera internal parameter matrix and a distortion coefficient.

When camera parameters are calibrated through a calibration plate, the calibration plate may have a preset pattern, such as a grid pattern or a black and white square pattern. The camera shoots an image of the calibration plate at a certain shooting distance, so that the image of the calibration plate can be compared with the pattern of the calibration plate, and the camera internal parameter matrix and the distortion parameter related to the shooting camera are obtained according to an offset of corresponding characteristic points in the image of the calibration plate and the pattern of the calibration plate in combination with the shooting distance.

It should be noted that, in some embodiments, the camera internal parameter matrix and the distortion coefficient may be pre-calibrated and pre-stored in a camera or an analysis device of biochip image, so that the analysis device can acquire the corresponding camera internal parameter matrix and the distortion coefficient from the camera, or determine the camera internal parameter matrix and the distortion coefficient according to the serial number or model number of the camera. Of course, in other embodiments, the analysis device may also detect the camera internal parameter matrix and the distortion coefficient of a corresponding camera each time before the image of the biochip is acquired, so that the validity of the camera internal parameter matrix and the distortion coefficient is ensured.

In some embodiments, a raw image is a fluorescent image of a biochip in which biochemical reaction has occurred.

After a biological sample to be detected is loaded on the biochip and biochemical reaction has occurred, a fluorescent image of the corresponding biochip may be collected using a particular equipment. It is understood that in the fluorescent image, the colors and intensities present by different reaction chambers may be the same or may be different.

In some embodiments, the preprocessed image includes a high frequency component image, and the step 41 includes: step 413 and step 414;

In step 413, performing Gaussian filtering on the biochip image to obtain a low-frequency component image; and In step 414, subtracting the low frequency component image from the biochip image to obtain a high frequency component image.

In this way, a low-frequency component image is obtained by Gaussian filtering, and then a high-frequency component image is obtained by subtracting a low-frequency component from the biochip image, so that high-frequency filtering is realized, and the problem of uneven fluorescent illumination of the micro chip is solved.

Of course, in other embodiments, the preprocessed image may not be limited to the high-frequency component image discussed above, and a grayscale image, a low-frequency component image, an edge detection image, and the like may be acquired according to practical requirements. The grayscale image may be obtained through image graying processing, the low-frequency component image may be obtained through low-frequency component extraction processing, and the edge detection image may be obtained through image edge extraction processing. In addition, the preprocessed image may also be obtained by performing one or several of the above processing methods in a preset order, which is not limited herein.

In some embodiments, the step 42 includes: step 421, step 422 and step 423;

In step 421, selecting a preset number of detection areas in a preprocessed image;

In step 422, detecting a center and radius of an area of interest in the detection area using Hough circle transform; and In step 423, making a circle according to the center and radius of the area of interest to determine the area of interest and segmenting the area of interest.

Taking the area of interest as the area where the reaction chambers are located in the image as an example, when the arrangement of the reaction chambers is detected, the positions of the reaction chambers in the detection area needs to be determined. Since the reaction chambers are generally circular, the detection of the center and radius of the chamber can be realized through Hough transform. Further, after the position of the reaction chamber is determined according to the center and radius of the chamber, the segmentation of the reaction chamber can be realized.

In some embodiments, the step 421 includes: selecting a corresponding detection area within a preset area of a preprocessed image.

The preset area may be set by a user according to experience, or automatically selected according to an algorithm. Of course, the detection area may also be a randomly selected area in the preprocessed image, which is not limited herein.

In some embodiments, the detection area is a rectangular area, and the detection area includes at least two rows or columns of partial areas of interest.

It is understood that when deflection correction is performed on the high-frequency component image to obtain a deflection corrected image, the deflection angle of the high-frequency component image needs to be determined. Since the reaction chambers on the biochip are generally disposed in arrays, i.e., the areas of interest are generally disposed in arrays, the detection of the image deflection angle can be realized through the arrangement direction of the chambers, and a rectangular area is favorable for determining a relative deflection angle between the long edge direction of the selected detection area and the arrangement direction of the reaction chambers.

That the detection area includes at least two rows or at least two columns of partial areas of interest can ensure the detection of the arrangement direction of the reaction chambers.

It should be noted that the size of the detection area may be flexibly configured according to the interval, radius and the like of the areas of interest, which is not limited herein.

Of course, in other embodiments, the shape of the detection area may not be limited to a rectangular shape discussed above, and other suitable shapes such as a square, a triangle, a circle, a parallelogram, etc. may be selected according to practical requirements, which is not limited herein.

In some embodiments, the preset number of detection areas selected each time may be multiple, and the directions of the multiple detection areas may be different, so as to improve the efficiency and accuracy of the image deflection angle detection. For example, the preset number of detection areas selected at a time may be 9.

In some embodiments, the step 42 includes: step 424, step 425 and step 426;

In step 424, performing expansion processing on a segmented image to connect adjacent areas of interest in a preset direction;

In step 425, performing principal component analysis on a largest contour in the detection area after the expansion processing to obtain a contour direction; and In step 426, determining an image deflection angle according to the contour direction to correct the preprocessed image to obtain a deflection corrected image.

Figure 15:
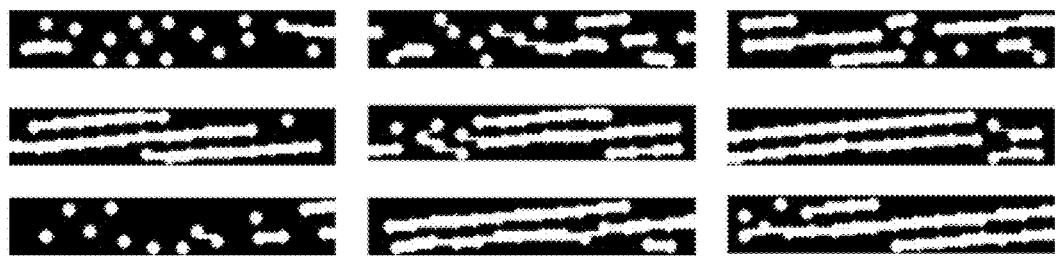
FIG. 15 is a schematic diagram of a contour after an expansion process has been performed on segmented reaction chambers according to an embodiment of the present application.

In step 424, the segmented areas of interest may be performed with expansion processing in the preset direction, so that the contours of the areas of interest extend in the preset direction, thus the contours of adjacent areas of interest are connected with each other. In one example, the preset direction may be a long edge direction of a rectangular detection area. FIG. 15 is a schematic diagram of a contour obtained by performing expansion processing on the areas of interest in 9 chambers in a preset direction in the case where the number of detection areas is 9.

After the contours of the areas of interest are connected, in step 425 the largest contour in the detection area is selected for PCA principal component analysis to obtain the contour direction. It is understood that, since the largest contour is generally formed by connecting a plurality of adjacent areas of interest, in one example, the obtained contour direction may serve as the arrangement direction of the reaction chambers. In particular, in the case of multiple detection areas, PCA principal component analysis may be performed on the largest contour in the multiple detection areas to obtain a contour direction.

Thus, in step 425 the image deflection angles of the biochip image and the preprocessed image may be determined according to the contour direction, and a deflection corrected image may be obtained by correcting the deflection angles of the biochip image and/or the preprocessed image.

In such way, the present disclosure can solve the problem of deflection angle detection by adjoining homodromous areas of interest to form a largest contour and then using PCA principal component analysis.

In some embodiments, the step 42 includes: step 427 and step 428;

In step 427, enlarging the selected area by a preset proportion and randomly reselecting a preset number of detection areas in the preprocessed image; and In step 428, detecting an image deflection angle repeatedly and iteratively until the image deflection angle is smaller than a preset angle threshold to obtain a deflection corrected image.

In such way, the image deflection angle is repeatedly and iteratively detected through detection areas of different sizes, so that accuracy of the image deflection angle is guaranteed.

In some embodiments, the preset angle threshold value range may be determined by the following conditional expression:

$$\cos\theta - (\max\{m, n\} - 1) \cdot \sin\theta > \frac{2\text{rad}}{dist}$$

where θ is a preset angle threshold, dist is an interval of the areas of interest, rad is a radius of the areas of interest, m is a row number of the areas of interest in the detection area, and n is a column number of the areas of interest in the detection area.

It should be noted that, in some embodiments, the biochip image may be precisely aligned by a hardware instrument device during photographing, so that the deflection corrected image can be determined directly from the biochip image photographed after precise alignment, and in this case, the process of detecting the deflection angle of the image may be omitted. In other embodiments, a flag bit may be disposed on a biochip entity. After the biochip image is obtained, a relative coordinate system may be constructed by identifying the flag bit on the biochip to obtain a deflection angle of the biochip with respect to the camera, and then obtain a deflection corrected image by correction.

Of course, the angle deflection correction may not be limited to the embodiments discussed above, and a suitable correction method may be selected according to actual situations, so that the analysis device may determine that the areas of interest on the chip satisfy relative positions in the lateral or longitudinal arrangement according to the deflection corrected image, which is not limited herein.

In some embodiments, the step 42 includes: step 427' and step 428'; In step 427', increasing the selected area by a preset proportion and randomly reselecting a preset number of detection areas in the preprocessed image; and In step 428', detecting an image deflection angle repeatedly and iteratively by a preset number of times to obtain a deflection corrected image.

In such way, the accuracy of the image deflection angle can also be guaranteed by detecting the image deflection angle repeatedly and iteratively for a preset number of times in detection areas of different sizes. In one example, the preset number may be preset by the system or by a user according to actual situations, for example, the preset number may be 6.

In some embodiments, the step 43 includes: step 431 and step 432;

In step 431, constructing a notch filter; and

In step 432, filtering the deflection corrected image by using the notch filter to obtain a periodic pattern enhanced image.

In such way, noise caused by surface dirt, sampling process and reaction process is weakened to a maximum extent by constructing the notch filter using the periodic pattern prior of the matrix biochip.

Figure 16:
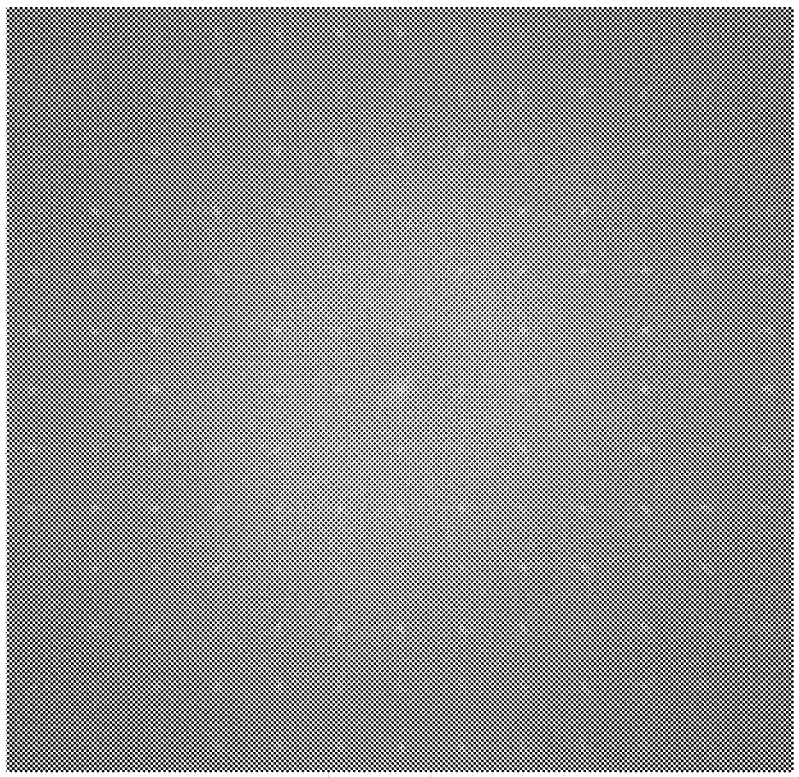
FIG. 16 is a schematic diagram of amplitude of Fourier transform of the biochip image into frequency domain according to an embodiment of the present application.
Figure 17:
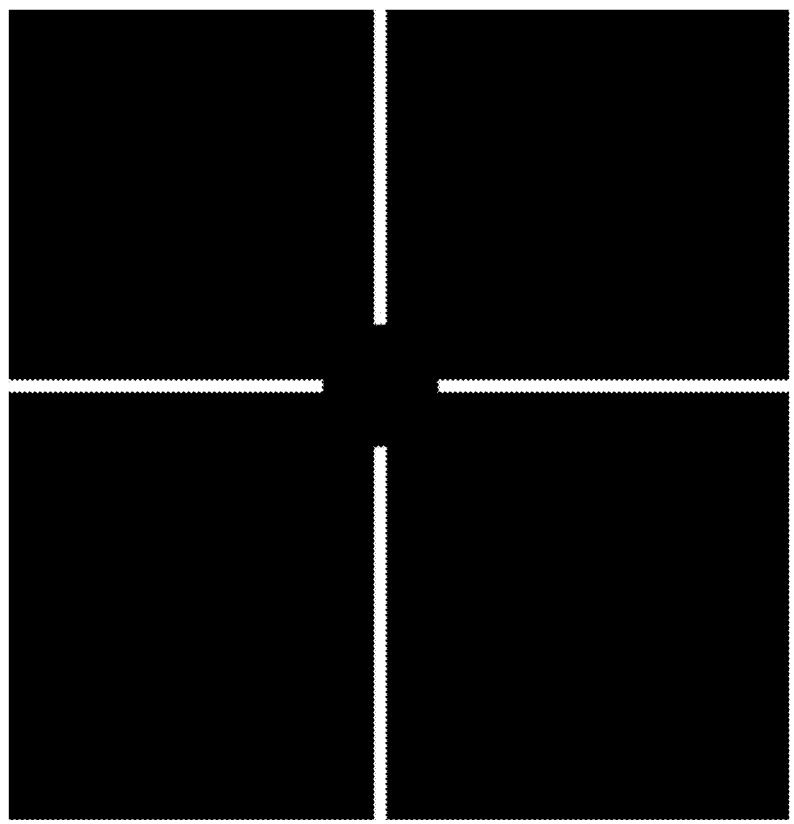
FIG. 17 is a schematic diagram of a filter according to an embodiment of the present application.

In one example, in an amplitude map obtained by Fourier transform of the biochip image into frequency domain as shown in FIG. 16, most image information is concentrated in the low frequency portion, therefore most image noise can be removed by filtering the image information in the central portion. Meanwhile, the information in the central vertical and central horizontal directions is the most easily filtered periodic pattern information. Thus, constructing the notch filter in step 431 may be adopted, as shown in FIG. 17, to remove image noise of a non-periodic pattern.

By adopting the notch filter, the complexity of time and space of the algorithm of the analysis method of the biochip image in the embodiments of the present disclosure is lower, the requirement on performance of the hardware equipment is looser, and therefore the cost is reduced and the operation efficiency is improved while ensuring the effect.

In some embodiments, the step 433 includes: step 4331, step 4332, and step 4333;

In step 4331, performing smooth filtering on a periodic pattern enhanced image by using a box filter;

In step 4332, integrating pixel values in a horizontal direction and a vertical direction of a smoothed image to obtain a first integral curve in the horizontal direction and a second integral curve in the vertical direction, and taking a minimum point set of the first integral curve and the second integral curve to determine a grid spacing line; and In step 4333, dividing grid areas according to the grid spacing line.

In such way, other noisy images in the image can be reduced by smoothing with a box filter, and further dividing grid areas.

In some embodiments, the length and width of an operator of the box filter satisfy the following conditional expression:

$$\left[\frac{dist}{2} - rad\right] < b < \left[\frac{dist}{2}\right]$$

where b is the length and width of the operator of the box filter, dist is an interval of the areas of interest, rad is a radius of the areas of interest.

In some embodiments, the step 43 includes: step 434 and step 435;

In step 434, detecting areas of interest in the deflection corrected image using Hough circle transform; and In step 435, drawing a circle according to the detected areas of interest to perform approximation so as to obtain grid areas through division.

That is to say, for the division of the grid areas, the areas of interest in the deflection corrected image may also be detected using Hough circle transform, and then a circle is drawn according to the detected areas of interest to perform approximation so as to obtain grid areas, thereby achieving the division of the grid areas.

Of course, the division of the grid areas may not be limited to the embodiments discussed above, and other division methods may also be adopted to perform division as needed, which is not limited herein.

In some embodiments, the step 44 includes: step 441 and step 442;

In step 441, traversing the grid areas, and calculating the mean variance of the pixel values of each grid area corresponding to the preprocessed image;

In step 442, marking a corresponding sample of area of interest as positive when the mean variance is greater than a variance threshold; and In step 443, marking a corresponding sample of area of interest as negative when the mean variance is not greater than the variance threshold.

In this way, by comparing the mean variance of pixel values of each grid with a variance threshold, division of the positive and negative is realized.

In some embodiments, the method of analyzing a biochip image includes: outputting a positive and negative identification result of the reaction chamber.

The analysis method of a biochip image according to an embodiment of the present disclosure can effectively identify a matrix biochip fluorescent image of high flux and low signal to noise ratio. Specifically, the problem of uneven fluorescent illumination of a micro chip is solved by high-frequency filtering; the problem of deflection angle detection is solved by performing PCA (principal component analysis) on the largest contour of adjoined homodromous chambers; noise caused by surface stains, a sample introduction process and a reaction process is weakened to the maximum extent by constructing a notch filter using periodic pattern prior of a matrix biochip, and chamber positioning and automatic analysis of sample positive and negative determination are successfully realized.

The following points need to be explained:

(1) The drawings of the embodiments of the present disclosure only relate to the structures related to the embodiments of the present disclosure, and other structures may refer to common designs.

(2) Without conflict, embodiments of the present disclosure and features of the embodiments may be combined with each other to arrive at new embodiments.

The above description is only a specific embodiment of the present disclosure, but the scope of the present disclosure is not limited thereto, and the scope of the present disclosure should be subject to the scope of the claims.

What is claimed is:

1. A chip loading structure comprising a loading plate body, wherein the loading plate body has an accommodating space configured to accommodate a detection chip;
   a first hollow area and at least one second hollow area, which penetrate to the accommodating space, are formed on a first plate surface of the loading plate body, wherein the first hollow area is configured to expose a reaction observation area of the detection chip from the first plate surface; and the at least one second hollow area is configured to expose at least one reagent port of the detection chip from the first plate surface; and
   the loading plate body is further provided with a connection portion which is detachably connectable to a transportation section in an analysis device, the transportation section being configured to transport the loading plate body;

wherein a first recess is disposed on the first plate surface at a position where the first hollow area is located, an area of an orthographic projection of the first recess on the first plate surface is larger than an area of an orthographic projection of the first hollow area on the first plate surface, and the orthographic projection of the first recess on the first plate surface completely covers the orthographic projection of the first hollow area on the first plate surface, and wherein the orthographic projection of the first recess on the first plate surface does not overlap with the orthographic projection of the second hollow area on the first plate surface.

2. The chip loading structure of claim 1, wherein a shape of the orthographic projection of the first hollow area on the first plate surface comprises a square, a rectangle, or a circle.

3. The chip loading structure of claim 1, wherein a plurality of second hollow areas are disposed by an interval along a first axis of the first plate surface, and in a case where the loading plate body is placed on the transportation section, a direction of the first axis is parallel to a first movement direction in which the transportation section moves into the analysis device.

4. The chip loading structure of claim 3, wherein a second recess is disposed on the first plate surface at a position where each of the second hollow areas is located an area of an orthographic projection of the second recess on the first plate surface is larger than an area of an orthographic projection of the second hollow area on the first plate surface, and the orthographic projection of the second recess on the first plate surface completely covers the orthographic projection of the second hollow area on the first plate surface.

5. The chip loading structure of claim 4, wherein in a case where the loading plate body is placed on the transportation section, an area of an orthographic projection of a second recess, which is rearwardly located in the first movement direction, on the first plate surface is larger than an area of an orthographic projection of a second recess, which is forwardly located in the first movement direction, on the first plate surface; the orthographic projection of the second recess, which is rearwardly located in the first movement direction, on the first plate surface is of an oval shape; and the orthographic projection of the second recess, which is forwardly located in the first movement direction, on the first plate surface has a circular shape.

6. The chip loading structure of claim 1, wherein the detection chip further has a heating electrode; and a third hollow area, which penetrates to the accommodating space, is disposed on the first plate surface to expose the heating electrode.

7. The chip loading structure of claim 6, wherein the third hollow area extends to a first side edge of the first plate surface; and the first side edge is perpendicular to a first axis of the first plate surface; and in a case where the loading plate body is placed on the transportation section, a direction of the first axis is parallel to a first movement direction in which the transportation section moves into the analysis device, and the first side edge is a side edge that is forwardly located in the first movement direction.

8. The chip loading structure of claim 1, wherein a receiving groove is disposed on a second plate surface of the loading plate body opposite to the first plate surface to form the accommodating space, and a protrusion structure is disposed on an inner side surface of the receiving groove to confine the detection chip within the receiving groove.

9. The chip loading structure of claim 8, wherein the protrusion structure comprises two groups of protrusions distributed at opposite sides of the first axis of the first plate surface, each group of protrusions comprising a plurality of protrusions spaced along the first axis, each protrusion protruding from the inner side surface of the receiving groove toward a direction approaching the first axis, so as to abut against a side surface of the detection chip in the receiving groove; and in a case where the loading plate body is placed on the transportation section, a direction of the first axis is parallel to a first movement direction in which the transportation section moves into the analysis device.

10. The chip loading structure of claim 8, wherein the receiving groove extends to a second side edge of the second plate surface; and the second side edge is perpendicular to a first axis of the first plate surface; and in a case where the loading plate body is placed on the transportation section, a direction of the first axis is parallel to a first movement direction in which the transportation section moves into the analysis device, and the second side edge is a side edge that is forwardly located in the first movement direction.

11. The chip loading structure of claim 1, wherein slot groups are respectively provided on two side surfaces at opposite sides of the first axis of the first plate surface of the loading plate body, each slot group comprising one or a plurality of slots spaced along the first axis, and the slots serve as the connection portion to be plugged with plug connectors in the transportation section in a one-to-one correspondence; and in a case where the loading plate body is placed on the transportation section, a direction of the first axis is parallel to a first movement direction in which the transportation section moves into the analysis device.

12. The chip loading structure of claim 11, wherein a socket in communication with the slot is disposed on a second plate surface of the loading plate body opposite to the first plate surface, to allow a corresponding plug connector to move into or out of the slot; a limiting protrusion is disposed on a side surface at a side of a second axis of the slot, and the limiting protrusion protrudes relative to the side surface toward a direction approaching the second axis, so as to confine the plug connector within the slot in a case where the plug connector moves to an interval position between the limiting protrusion and a bottom surface of the slot opposite to the limiting protrusion; and the second axis of the slot is parallel to a movement direction in which the plug connector moves into or out of the slot.

13. An analysis device, comprising: a loading section, a transportation section, a temperature control section and a signal detection section, wherein, the loading section adopts the chip loading structure of claim 1 to carry a detection chip, and is detachably connectable to the transportation section;

the transportation section is configured to transport the chip loading structure;

the temperature control section comprises a heater and a cooler, wherein the heater is configured to heat the detection chip, and the cooler is configured to cool the detection chip; and the signal detection section comprises an optical sensor configured to receive light from the detection chip and perform detection according to the light.

14. The analysis device of claim 13, wherein the transportation section comprises:
a transportation structure configured to bear the chip loading structure, and able to be at least partially driven; and
a driver configured to drive the transportation structure to cause the chip loading structure to reciprocate among a first position, a second position, and a third position,
wherein the first position allows the chip loading structure to be received in the transportation structure;
the second position allows the temperature control section to adjust a temperature of the detection chip; and
the third position allows the optical sensor of the signal detection section to receive the light from the detection chip.

15. The analysis device of claim 14, wherein the transportation structure comprises:
an objective table configured to, in use, bear the chip loading structure;
a movable platform configured to be connected to the driver to move under drive of the driver; and
a support configured to connect the objective table and the movable platform, so that the objective table is driven along with the movable platform.

16. The analysis device of claim 15, wherein,
slot groups are respectively provided on two side surfaces at opposite sides of the first axis of the first plate surface of the loading plate body, each slot group comprising one or a plurality of slots spaced along the first axis, and the slots serve as the connection portion to be plugged with plug connectors in the transportation section in a one-to-one correspondence; and in a case where the loading plate body is placed on the transportation section, a direction of the first axis is parallel to a first movement direction in which the transportation section moves into the analysis device;
a mounting groove adapted to accommodate the loading plate body is disposed on a bearing surface of the objective table, and a mounting groove opening in communication with the mounting groove is disposed on a first side surface of the objective table to allow the loading plate body to move into or out of the mounting groove, the first side surface being perpendicular to a first movement direction in which the objective table moves into the analysis device, and the first side surface is a side surface facing backwards in the first movement direction; and
the plug connectors, which protrude from the side surface of the mounting groove toward a direction approaching a third axis of the mounting groove, are disposed on the objective table, the third axis being parallel to the first movement direction.

17. The analysis device of claim 15, wherein,
the detection chip further has at least one heating electrode;
a third hollow area, which penetrates to the accommodating space, is disposed on the first plate surface to expose the at least one heating electrode;
the heater comprises at least one contact electrode configured to, in use, be in electrical contact with the at least one heating electrode of the detection chip in one-to-one correspondence; and
the heater is further configured to apply an electrical signal to the heating electrode of the detection chip through the contact electrode, so that the heating electrode heats the detection chip.

18. The analysis device of claim 17,
wherein the contact electrode is fixed on a bearing surface of the objective table and is located at a side of the mounting groove opposite to the mounting groove opening; one end of the contact electrode protrudes relative to a side surface of the mounting groove in a direction opposite to a first movement direction in which the objective table moves into the analysis device; the contact electrode is provided with a contact portion which is adapted to be in electrical contact with the heating electrode; the contact portion protrudes relative to a surface of the contact electrode opposite to the heating electrode toward a direction approaching the heating electrode; and the heater further comprises an elastic piece, which is respectively connected to the contact electrode and the objective table, to apply a pulling force to the contact electrode toward the bearing surface of the objective table; or
wherein an electrode slot is provided on a bearing surface of the objective table, the contact electrode is inserted in the electrode slot, and the contact electrode is fixedly connected to the objective table by a fastener.

19. The analysis device of claim 13, wherein the signal detection section further comprises:
a light source configured to, in use, provide light to illuminate the detection chip;
a light transmission portion configured to, in use, transmit the light provided by the light source to the detection chip and transmit light emitted by the detection chip to the optical sensor; and
a bracket configured to fix and bear the light source and the light transmission portion, wherein a focal length adjustment structure is disposed on the bracket and configured to adjust a distance between the light transmission portion and the detection chip, such that the detection chip is positioned at a focus of the light transmission portion; and the focal length adjustment structure has a focal length adjustment knob and a knob extension connected to the focal length adjustment knob, the knob extension extending to a side close to the light transmission portion to facilitate manual adjustment.

20. An analysis system, comprising:
the analysis device of claim 13; and
the detection chip.

* * * * *